United States Patent [19]
Kriesel et al.

[11] Patent Number: 5,649,910
[45] Date of Patent: Jul. 22, 1997

[54] FLUID DELIVERY APPARATUS AND METHOD OF MAKING SAME

[75] Inventors: Marshall S. Kriesel, St. Paul; Steven M. Arnold, Minnetonka; James M. Garrison, South Minneapolis; Farhad Kazemzadeh, Bloomington, all of Minn.; William J. Kluck, Hudson, Wis.; Steven C. Barber, Shorewood, Minn.

[73] Assignee: Science Incorporated, Bloomington, Minn.

[21] Appl. No.: 473,649

[22] Filed: Jun. 6, 1995

Related U.S. Application Data

[63] Continuation-in-part of Ser. No. 46,438, May 18, 1993, Pat. No. 5,411,480, which is a continuation-in-part of Ser. No. 987,021, Dec. 7, 1992, Pat. No. 5,279,558, which is a continuation-in-part of Ser. No. 870,269, Apr. 17, 1992, Pat. No. 5,205,820, which is a continuation-in-part of Ser. No. 642,208, Jan. 16, 1991, Pat. No. 5,169,389, which is a continuation-in-part of Ser. No. 367,304, Jun. 16, 1989, Pat. No. 5,019,047.

[51] Int. Cl.6 .................................................. A61M 37/00
[52] U.S. Cl. ............................. 604/133; 604/85; 604/153; 604/890.1; 128/DIG. 12
[58] Field of Search .......................... 604/8, 9, 131, 604/132, 133, 140, 153, 167, 247

[56] References Cited

U.S. PATENT DOCUMENTS

| | | | |
|---|---|---|---|
| 4,152,098 | 5/1979 | Moody et al. | 604/153 X |
| 4,637,103 | 1/1987 | Hutzenlaub | 26/73 |
| 4,815,181 | 3/1989 | Dornier et al. | 26/91 |
| 5,014,402 | 5/1991 | Cunningham | 26/91 |
| 5,341,547 | 8/1994 | Rutz | 26/72 |
| 5,355,564 | 10/1994 | Gunter, Jr. et al. | 26/94 |

FOREIGN PATENT DOCUMENTS

3113282C2  10/1982  Germany.

*Primary Examiner*—Sam Rimell
*Assistant Examiner*—Robert V. Racunas
*Attorney, Agent, or Firm*—James E. Brunton

[57] ABSTRACT

An apparatus for accurately infusing medicinal agents into an ambulatory patient at specific rates over extended periods of time. The apparatus is of a compact, low profile, laminate construction and includes an elastic distendable membrane, which, in cooperation with a thin planar base defines a fluid chamber having a fluid outlet. Disposed within the fluid chamber is a thin fluid permeable member which precisely controls the rate of fluid flow through the fluid outlet. The apparatus also includes a highly novel fluid flow indicator that provides a readily discernible visual indication of fluid flow through the apparatus.

30 Claims, 18 Drawing Sheets

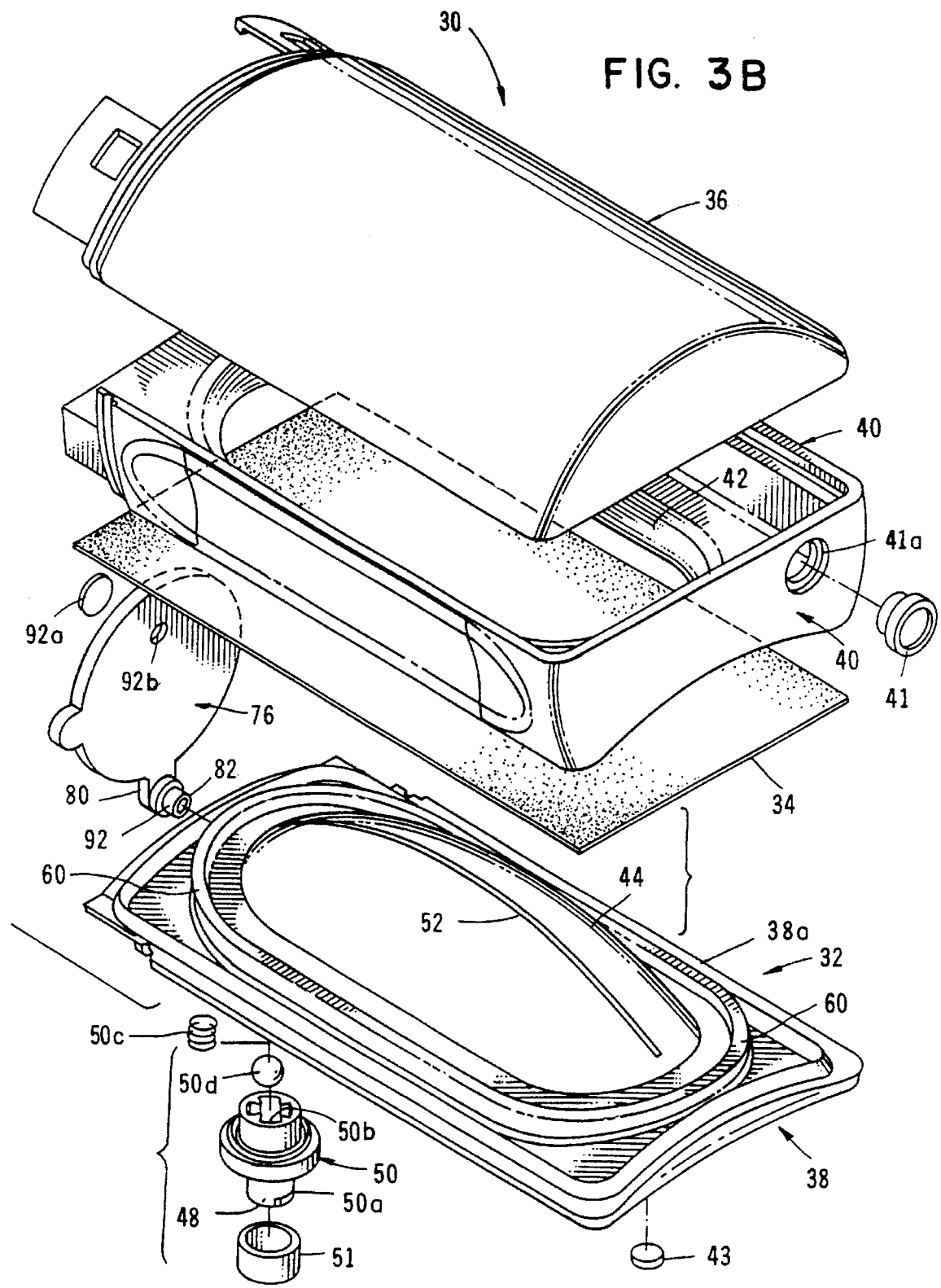

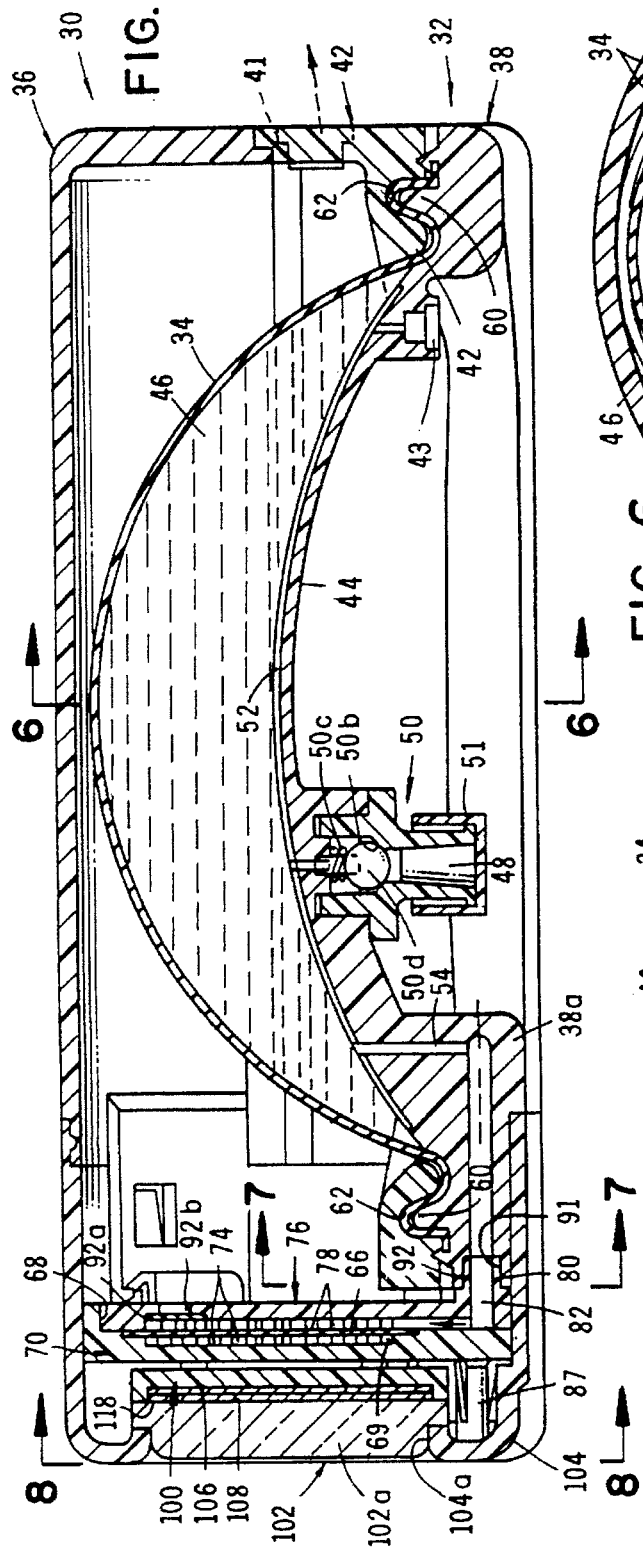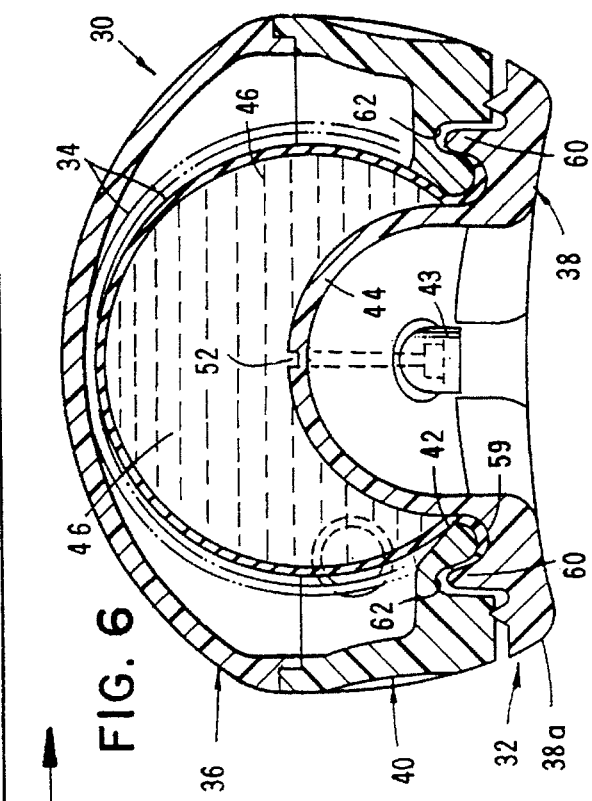

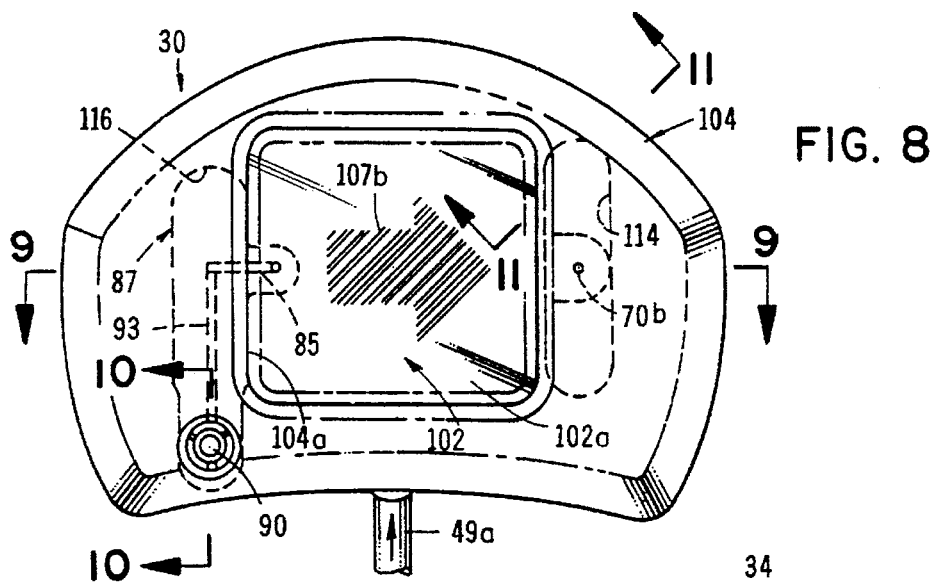
FIG. 8
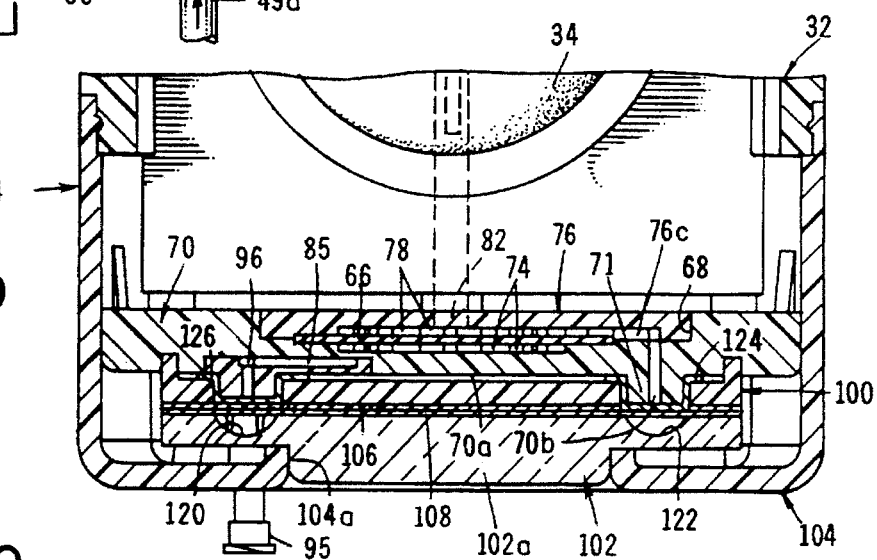
FIG. 9
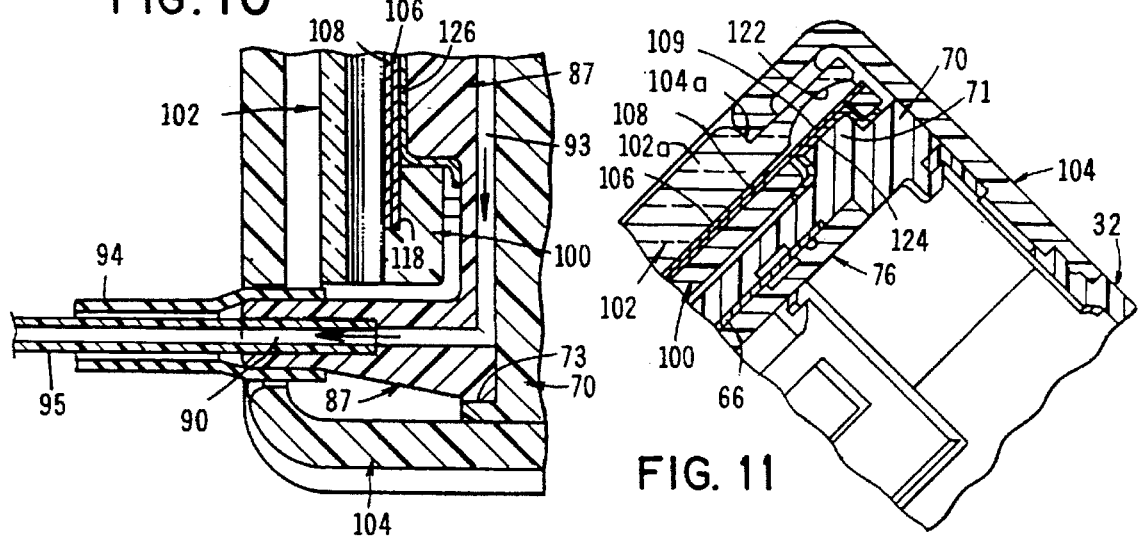
FIG. 10
FIG. 11

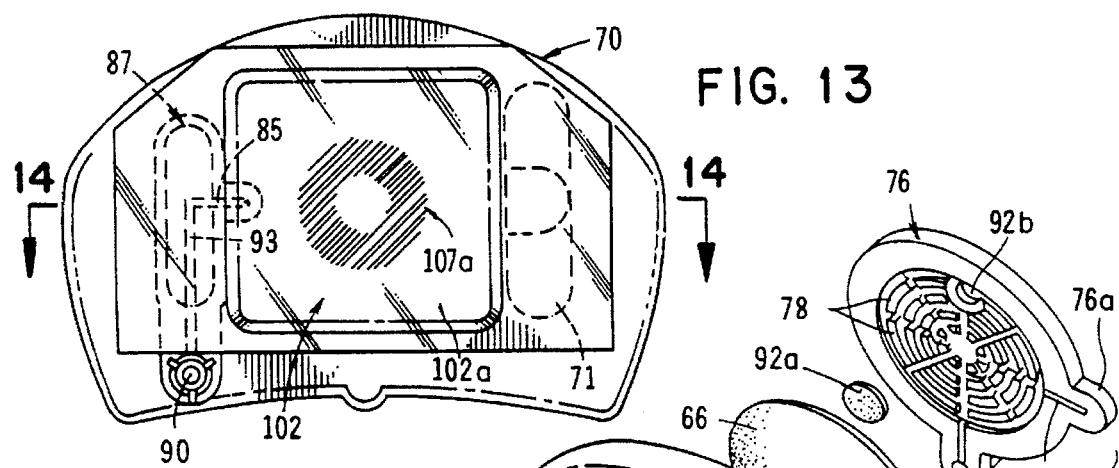
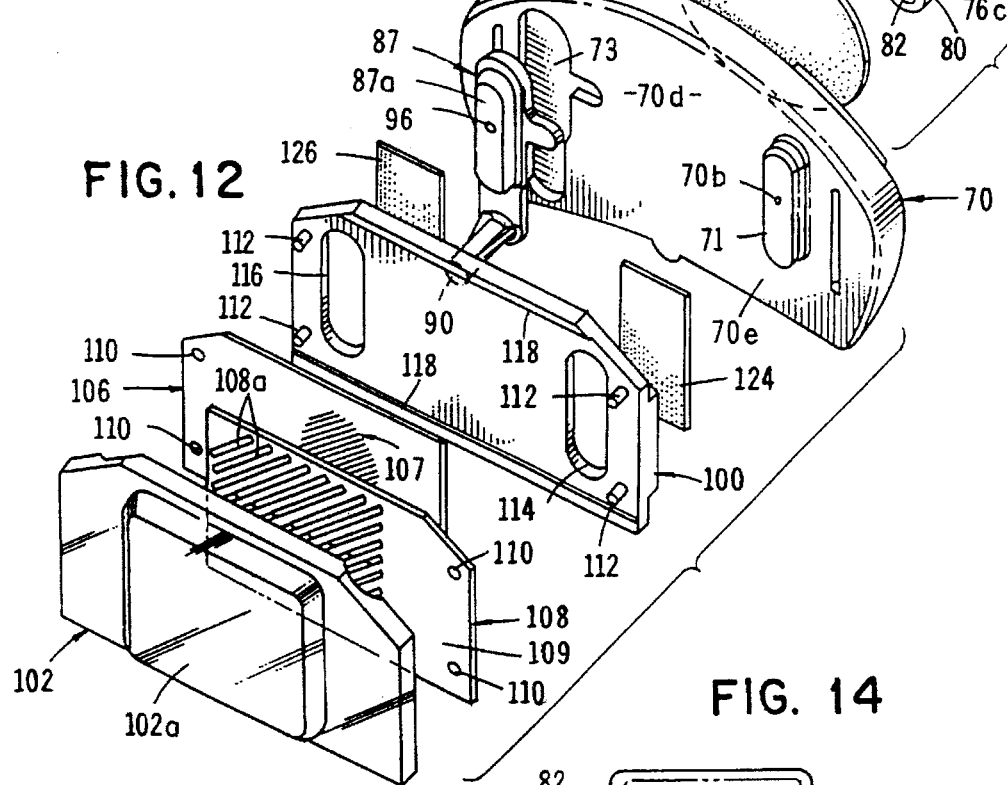
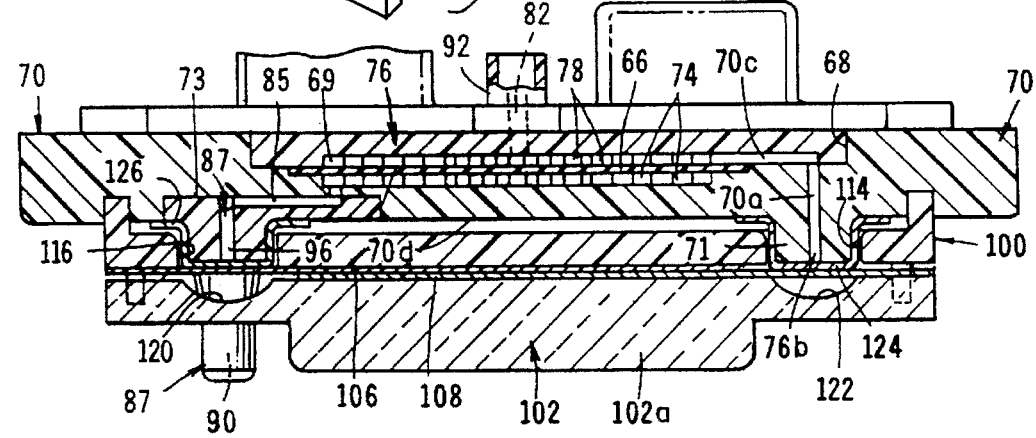

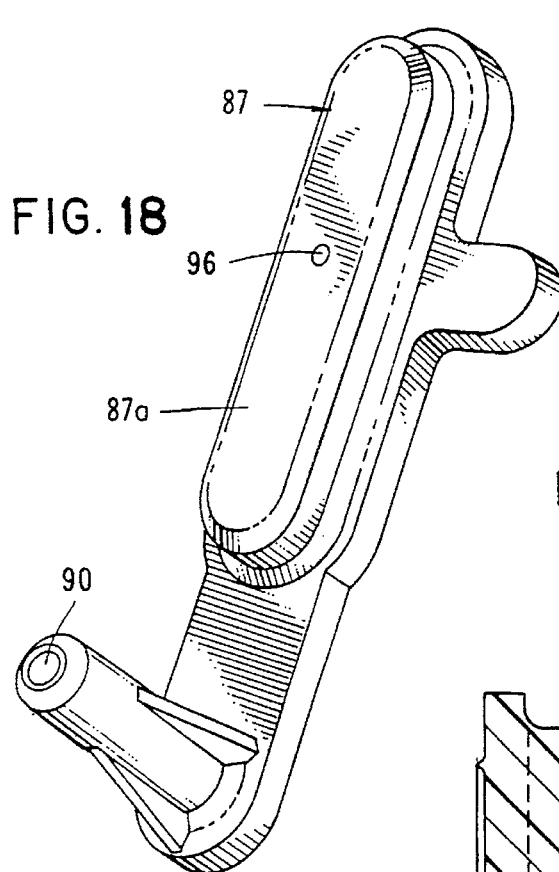
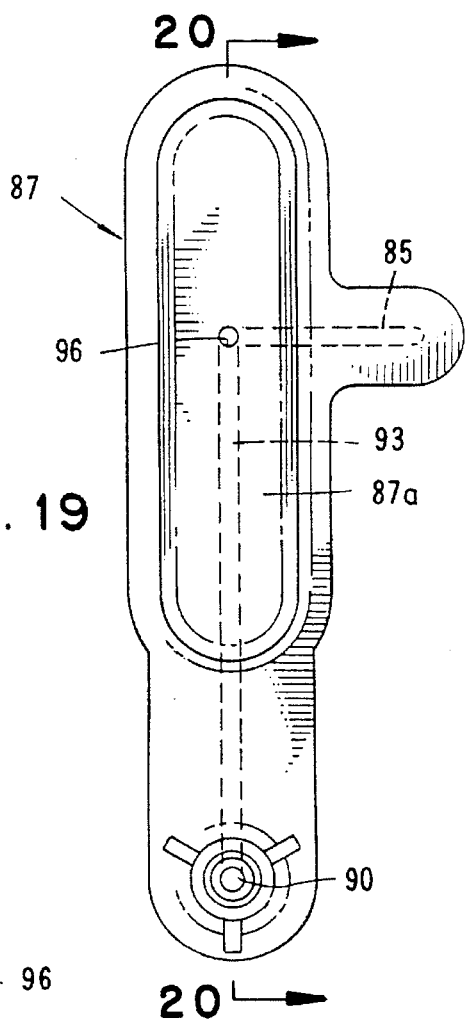
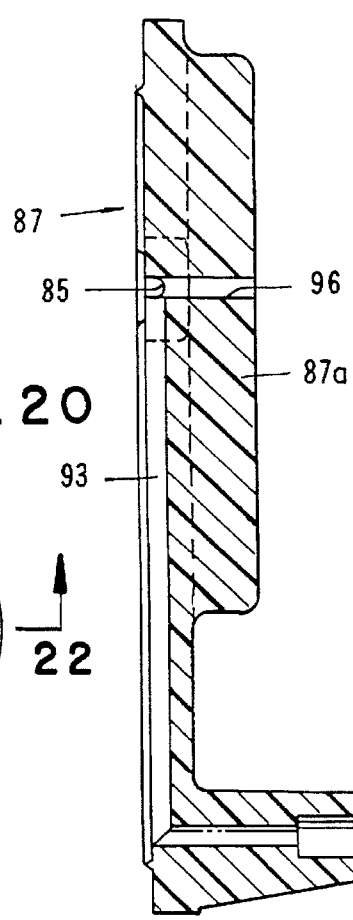
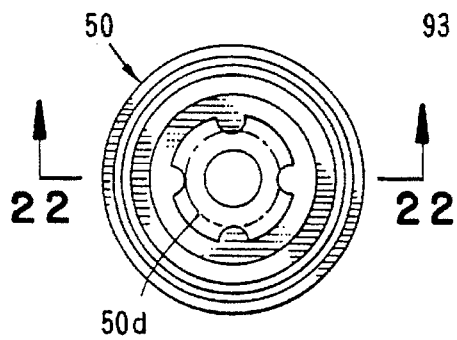
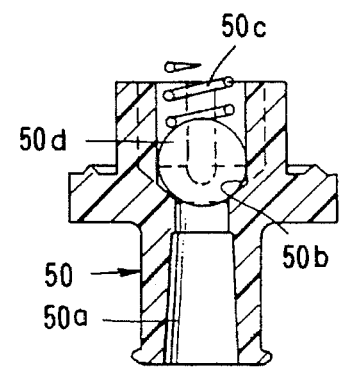
FIG. 18
FIG. 19
FIG. 20
FIG. 21
FIG. 22

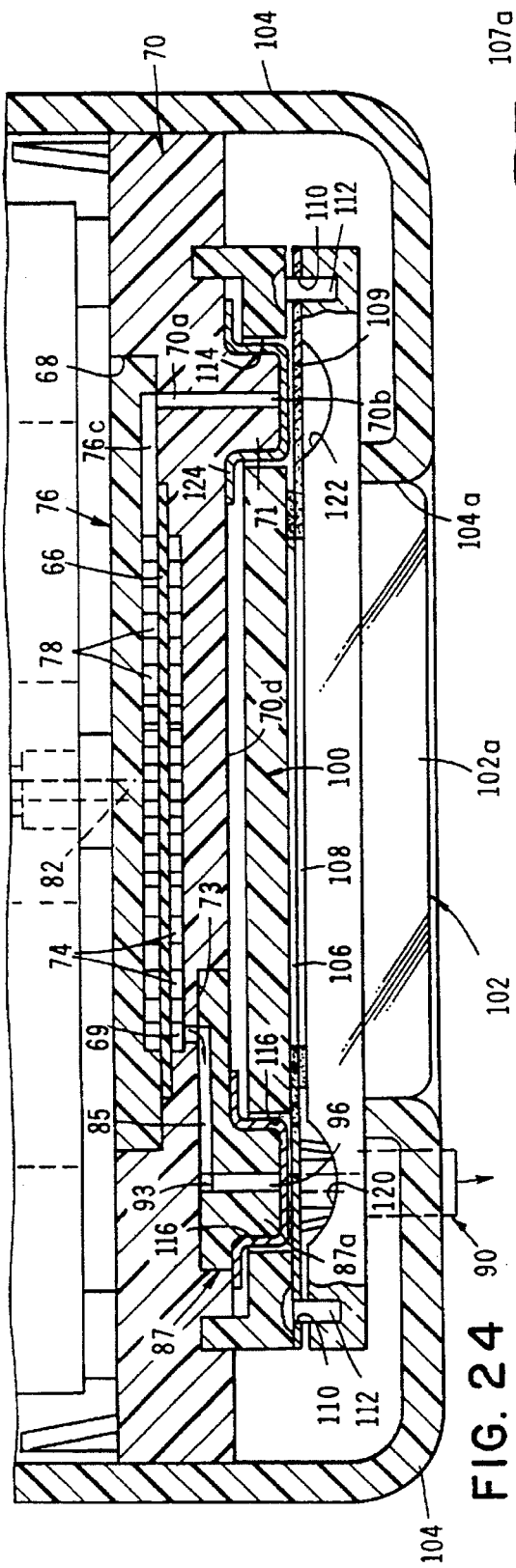
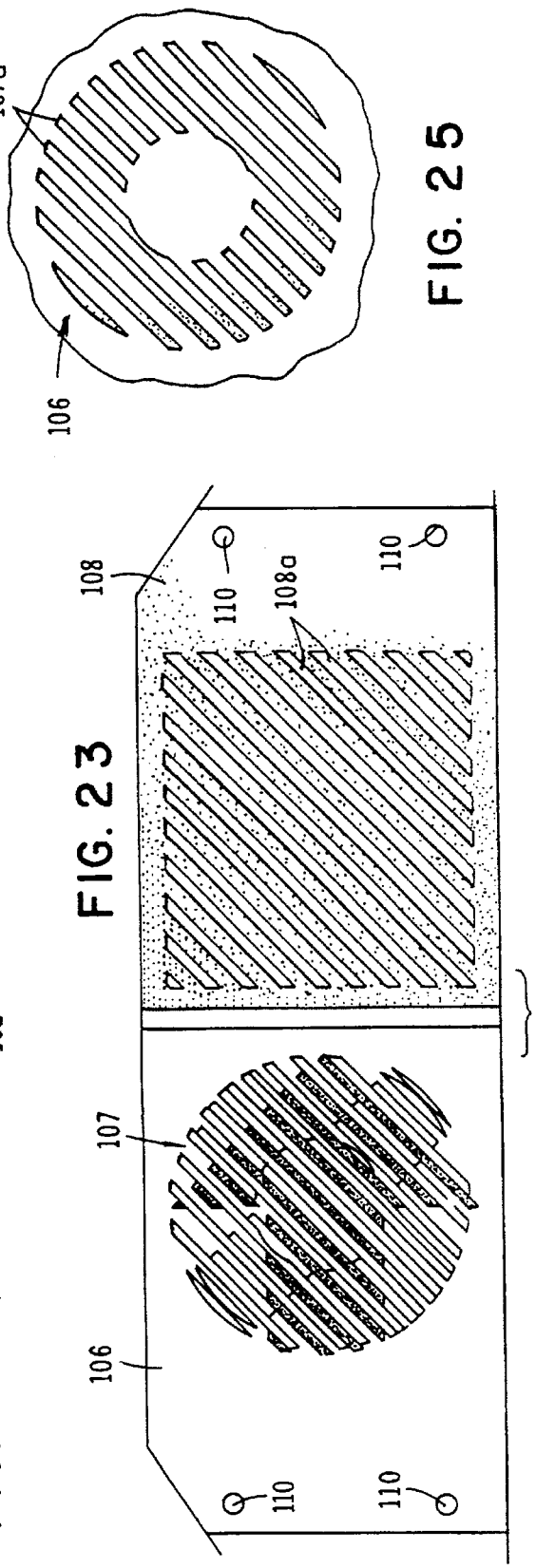
FIG. 23
FIG. 24
FIG. 25

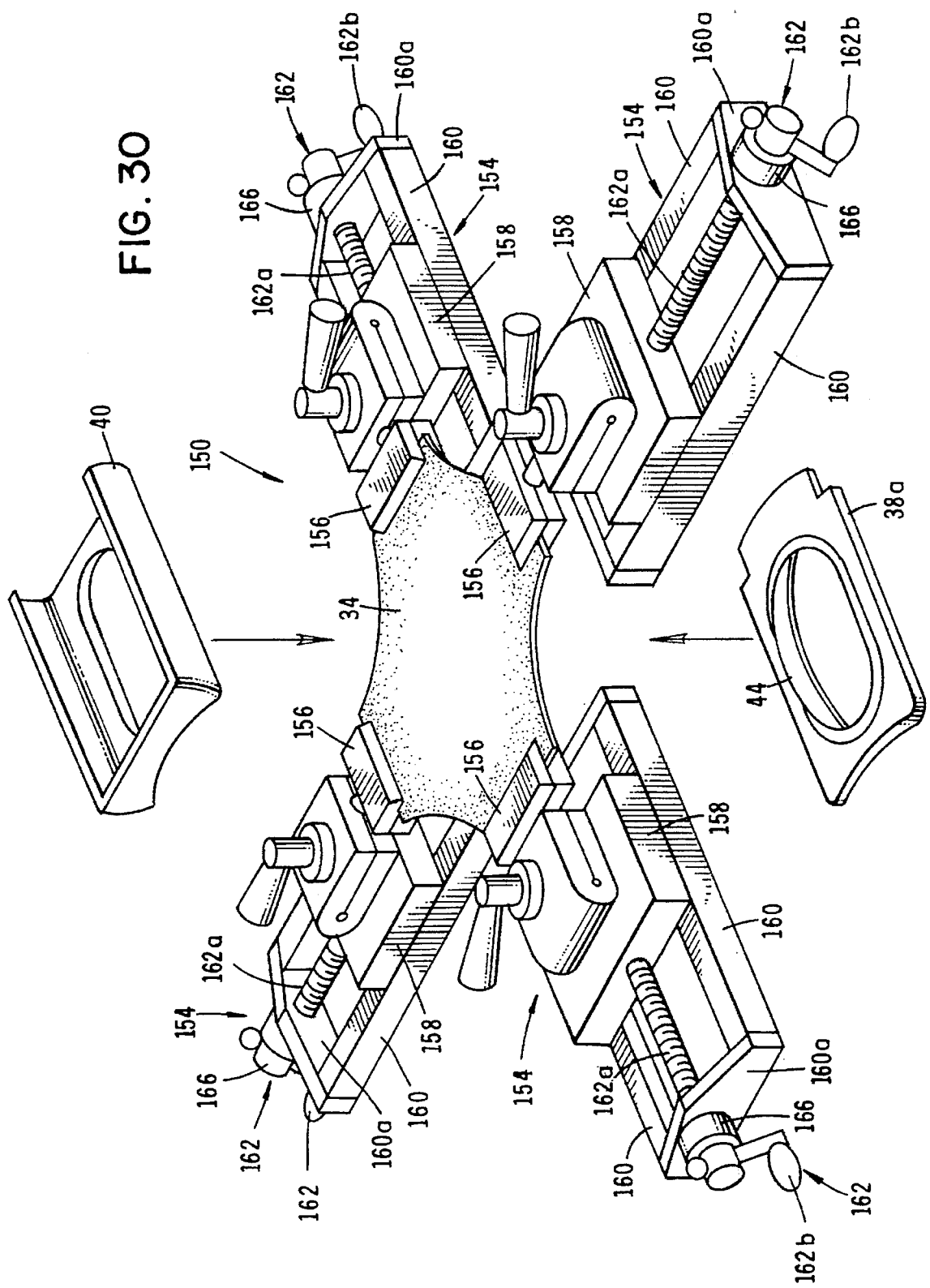

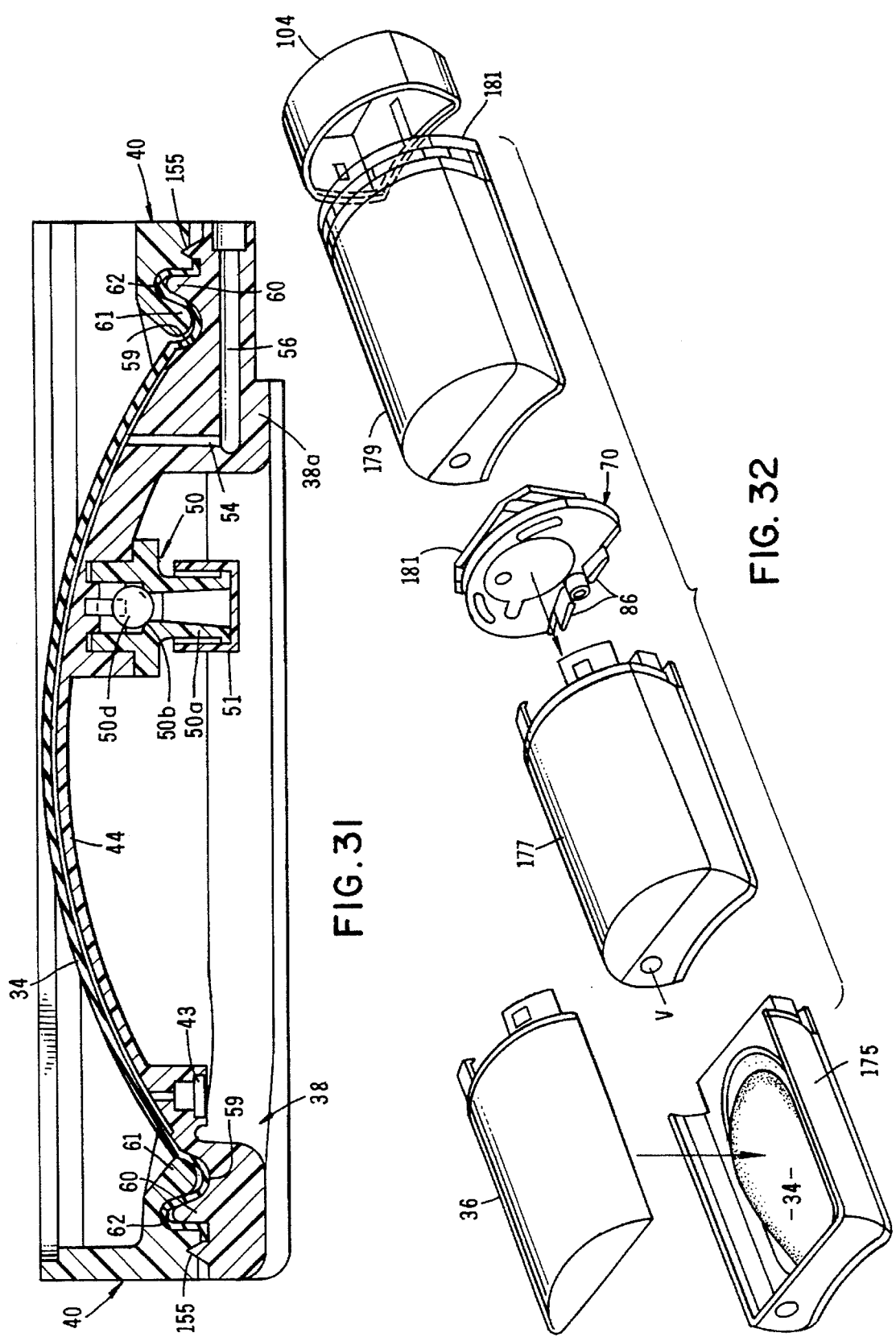

FLUID DELIVERY APPARATUS AND METHOD OF MAKING SAME

BACKGROUND OF THE INVENTION

This is a continuation in part application of a co-pending application filed May 1, 1995 which is a continuation in part of application, Ser. No. 08/046,438, filed May 18, 1993 now U.S. Pat. No. 5,411,480; which is a continuation in part of application Ser. No. 07/987,021 which has now issued into U.S. Pat. No. 5,279,558; which is a continuation in part of application Ser. No. 07/870,269 which has now issued into U.S. Pat. No. 5,205,820; and which is, in turn, a continuation in part of application Ser. No. 07/642,208 which has now issued into U.S. Pat. No. 5,169,389; which is a continuation in part of application Ser. No. 07/367,304 Filed Jun. 16, 1989 which has now issued into U.S. Pat. No. 5,019,047

1. Field of the Invention

The present invention relates generally to fluid delivery devices. More particularly, the invention concerns an improved apparatus, including visual flow indicator means, for infusing medicinal agents into an ambulatory patient at specific rates over extended periods of time.

2. Discussion of the Invention

Many medicinal agents require an intravenous route for administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus.

Devices from which liquid is expelled from a relatively thick-walled bladder by internal stresses within the distended bladder are well-known in the prior art. Such bladder, or "balloon" type, devices are described in U.S. Pat. No. 3,469,578, issued to Bierman and in U.S. Pat. No. 4,318,400, issued to Perry. The devices of the aforementioned patents also disclose the use of fluid flow restrictors external of the bladder for regulating the rate of fluid flow from the bladder.

The prior art bladder type infusion devices are not without drawbacks. Generally, because of the very nature of bladder or "balloon" configuration, the devices are unwieldy and are difficult and expensive to manufacture and use. Further, the devices are somewhat unreliable and their fluid discharge rates are frequently imprecise.

The apparatus of the present invention overcomes many of the drawbacks of the prior art by eliminating the bladder and making use of recently developed elastomeric films and similar materials, which, in cooperation with a base, define a fluid chamber that contains the fluid which is to be dispensed. The elastomeric film membrane controllably forces fluid within the chamber into fluid flow channels provided in the base.

The elastomeric film materials used in the apparatus of the present invention, as well as various alternate constructions of the apparatus, are described in detail in U.S. Pat. No. 5,205,820 issued to the present inventor. Therefore, U.S. Pat. No. 5,205,820 is hereby incorporated by reference in its entirety as though fully set forth herein. Co-pending U.S. Ser. No. 08/046,438 filed by the present inventor on May 18, 1993 also describes various alternate constructions and modified physical embodiments of the invention. This co-pending application is also hereby incorporated by reference in its entirety as though fully set forth herein.

The apparatus of the present invention can be used with minimal professional assistance in an alternate health care environment, such as the home. By way of example, devices of the invention can be comfortably and conveniently removably affixed to the patient's body and can be used for the continuous infusion of antibiotics, hormones, steroids, blood clotting agents, analgesics, and like medicinal agents. Similarly, the devices can be used for I–V chemotherapy and can accurately deliver fluids to the patient in precisely the correct quantities and at extended microfusion rates over time.

One of the embodiments of the invention described in continuation in part application Ser. No. 08/046,4,38 includes a highly novel, laminate stored energy means made up of a plurality of individual membranes. As before, this unique stored energy means cooperates with the base to define one or more fluid reservoirs or chambers. However, by constructing the stored energy means from a composite of several elements or layers, the elastic characteristics of the stored energy means can be precisely tailored and the stored energy means can be uniquely constructed to function also as a gas permeability valve as well as the means for expelling fluids from the fluid reservoir. This unique, multilayered or gradient construction may permit venting to atmosphere through the membrane surface certain selected, entrained gases or vapors in the reservoir while simultaneously precluding any negative migration of selected atmospheric gases or vapors into the reservoir. Where the composite is made up of two or more layers of alternating thickness and permeability, and the permeability constants of the individual film layers are pressure dependent, the permeability of the stored energy means is effected and the direction of flow of the permeant through the membrane wall is controlled by the order in which the individual layers or gradations of the composite are assembled.

The embodiments of the invention described in U.S. Ser. No. 08/046,438 also include an embodiment wherein the rate of fluid flowing from the dispensing means of the device is controlled by flow control means disposed intermediate the reservoir outlet and the fluid dispensing port of the device. More particularly, the flow rate control means comprises a fluid flow micro-conduit and a porous member which functions to restrict the flow of fluid between the outlet and the dispensing port. The embodiments of the invention described herein include different forms of flow control means and also include novel flow identification means.

SUMMARY OF THE INVENTION

It is an object of the present invention to provide an apparatus for expelling fluids at a precisely controlled rate which is of a compact, low profile, laminate construction. More particularly, it is an object of the invention to provide such an apparatus and the method of making the same, which can be used for the precise infusion of pharmaceutical fluids to an ambulatory patient at controlled rates over extended periods of time.

It is another object of the invention to provide an apparatus of the aforementioned character which is highly reliable and easy-to-use by lay persons in a non-hospital environment.

Another object of the invention is to provide an apparatus which can be factory prefilled with a wide variety of medicinal fluids or one which can readily be filled in the field shortly prior to use.

A further object of the invention is to provide a low profile, fluid delivery device of laminate construction which can be manufactured inexpensively in large volume by automated machinery.

Another object of the invention is to provide a device of the aforementioned character which includes a novel rate control membrane disposed intermediate the fluid reservoir outlet and the outlet port of the device.

Another object of the invention is to provide a device of the character described which embodies a highly novel fluid flow indicator that provides a readily discernible visual indication of fluid flow status through the device.

Another object of the invention is to provide an apparatus of the aforementioned character in which the stored energy source is of a novel laminate construction which can be precisely tailored to deliver fluid from the device at precise rates.

Another object of the invention is to provide a method of making a device of the character described in the preceding paragraphs in which the elastomeric membrane is pre-stressed and then connected to the base in a sealable manner.

Other objects of the invention are set forth in U.S. Pat. No. 5,205,820 which is incorporated herein and still further objects will become more apparent from the discussion which follows.

By way of summary, the fluid delivery apparatus of the present form of the invention comprises three cooperating subassemblies, namely a reservoir assembly, a fluid flow control subassembly and a flow indicator subassembly. The reservoir subassembly, which readily lends itself to automated manufacture, is generally similar to that described in copending Ser. No. 08/046,438 and includes a base and a stored energy means comprising at least one distendable elastomeric membrane which cooperates with the base to form a fluid reservoir. The fluid flow control subassembly is also similar to that described in Ser. No. 08/046,438 in that it comprises a thin permeable flow control membrane which controls the rate of flow of fluid flowing toward the outlet port of the device.

However, in the present embodiment of the invention, the flow control membrane is not disposed within the reservoir, but rather resides exteriorly thereof. The highly novel fluid flow indicator means of the invention comprises a mechanical fluid flow indicator that provides a clear visual indication of normal fluid flow and absence of fluid flow either because the reservoir is empty or because the flow lines are occluded. More particularly, symbols indicating the operating condition of the device are produced by the movement of thin, indicia-carrying films. These films, which comprise a part of the flow indicator means, are shifted by the movement of mechanical actuators which are deflected solely by the fluid pressure within the device. The fluid flow indicator design does not invade the fluid flow path and yet utilizes the same stored energy means to generate fluid pressure that provides for the normal functioning of the device. The fluid flow indicator is highly reliable in operation, can be produced inexpensively, and, because it has very few parts, is easy to manufacture.

BRIEF DESCRIPTION OF THE DRAWINGS

FIG. 3B is a generally perspective, exploded view of the remainder of the flow control means along with the reservoir subassembly portion of one form of the fluid dispenser apparatus of the invention shown in FIGS. 1 and 2.

FIG. 5 is a cross-sectional view taken along lines 5—5 of FIG. 4.

FIG. 6 is a cross-sectional view taken along lines 6—6 of FIG. 5.

FIG. 7 is a cross-sectional view taken along lines 7—7 of FIG. 5.

FIG. 8 is a view of the apparatus taken along lines 8—8 of FIG. 5.

FIG. 9 is a cross-sectional view taken along lines 9—9 of FIG. 8.

FIG. 10 is a cross-sectional view taken along lines 10—10 of FIG. 8.

FIG. 11 is a cross-sectional view taken along lines 11—11 of FIG. 8.

FIG. 12 is a generally perspective, exploded view of one form of forward housing portion of the apparatus of the invention which is also shown on the left-hand portion of FIG. 3.

FIG. 13 is a front view of the housing portion.

FIG. 14 is a cross-sectional view taken along lines 14—14 of FIG. 13.

FIG. 18 is a generally perspective view of the output port of the apparatus.

FIG. 19 is a front view of the output port shown in FIG. 18.

FIG. 20 is a cross-sectional view taken along lines 20—20 of FIG. 19.

FIG. 21 is a front view of the luer valve fitting of the apparatus.

FIG. 22 is a cross-sectional view taken along lines 22—22 of FIG. 21.

FIG. 23 is an enlarged plan view of the indicia carrying thin films of the apparatus of the invention.

FIG. 24 is a cross-sectional view similar to FIG. 14 showing the indicator means of the invention in its starting configuration.

FIG. 25 is a fragmentary plan view of the symbol that is viewable by the user when the apparatus is in the configuration shown in FIG. 24.

FIG. 30 is a generally perspective, exploded view of one type of apparatus for carrying out the first step of one form of the method of the invention.

FIG. 31 is a cross-sectional view of the base portion of the device illustrating the second step of one form of the method of the invention.

FIG. 32 is a generally perspective exploded view showing the next sequential steps of one form of the method of the invention.

FIG. 34A is an enlarged cross-sectional view taken along lines 34A—34A of FIG. 34 showing the membrane gripper means of the tenter frame apparatus.

DESCRIPTION OF THE INVENTION

Figure 1:
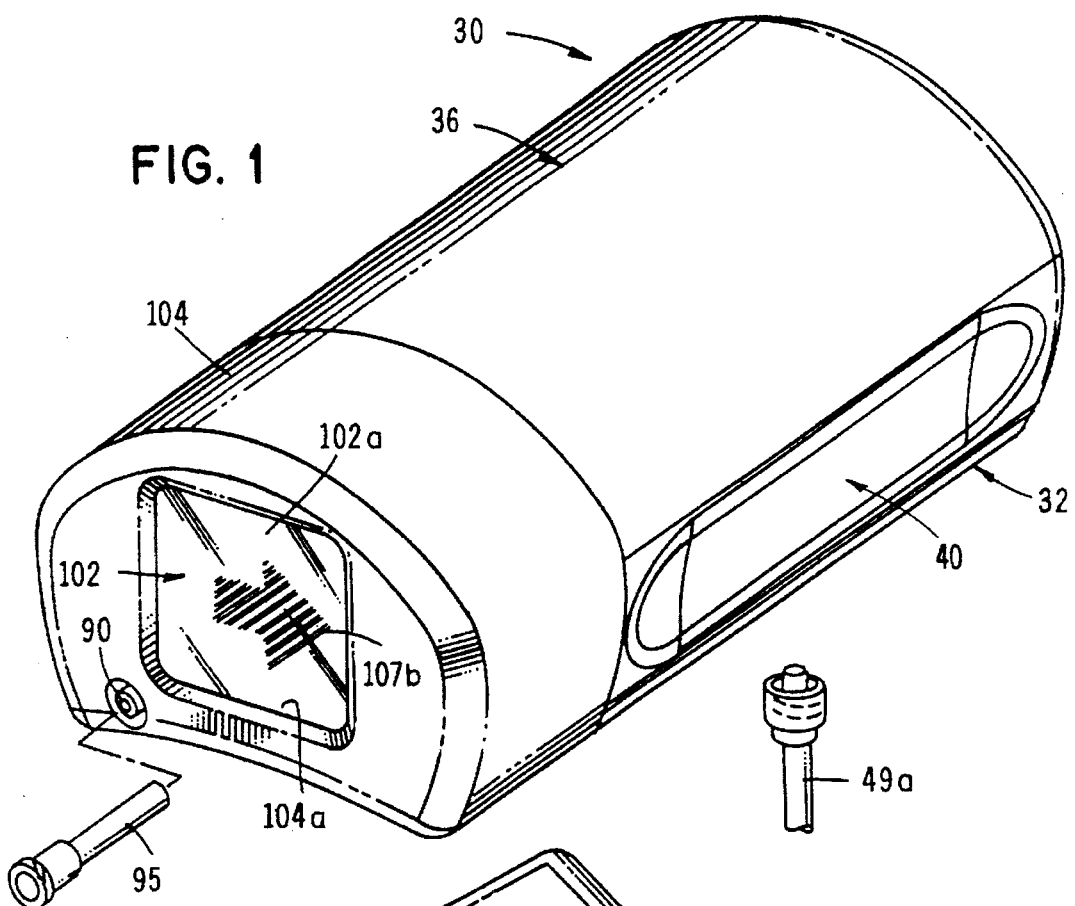
FIG. 1 is a generally perspective top view of one form of the fluid delivery apparatus of the invention.
Figure 2:
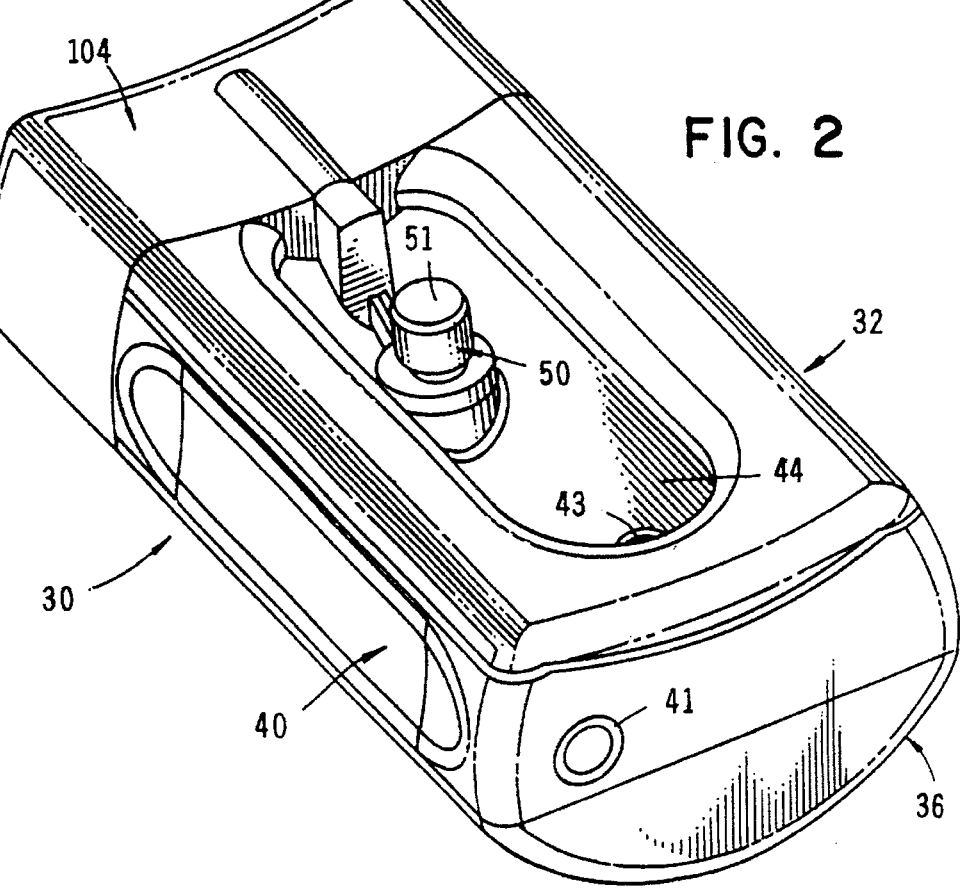
FIG. 2 is a generally perspective, bottom view of the apparatus shown in FIG. 1.

Referring to the drawings and particularly to FIGS. 1 through 7, the apparatus of this latest form of the present invention is there illustrated and identified generally by the numeral 30. As best seen in FIGS. 3A and 3B, the apparatus comprises three major cooperating subassemblies namely, a reservoir subassembly, a flow rate control subassembly, and a flow indicator subassembly. These subassemblies will be discussed in detail in the paragraphs which follow.

Considering first the reservoir subassembly shown in FIG. 3B, this subassembly is similar in many respects to that described in Ser. No. 08/046,438 and includes a base assembly 32, a stored energy source, or distendable membrane assembly 34, and a cover 36 for enclosing the stored energy source and the base assembly (see also FIGS. 1 and 2). The base assembly includes an ullage defining means, shown here as substrate 38 and a membrane capture housing 40 having a bottom opening 42 which receives the distendable membrane engaging element or protuberance 44 (see also FIG. 5).

Referring particularly to FIGS. 3B and 5, the ullage substrate 38 comprises, in addition to the distendable member engaging protuberance, or ullage, 44, filling means which enables filling of the fluid reservoir which is formed between protuberance 44 and distended membrane 34. This filling means here comprises a fluid inlet 48 provided in a luer valve fitting 50, the character of which will presently be described. Protuberance 44 is provided with a longitudinally extending fluid passageway 52 (FIG. 3B) which communicates with fluid passageways 54 and 56 provided in the base portion 38a of ullage substrate 38 (see also FIGS. 5 and 7).

Base portion 38a of ullage substrate 38 also includes an upstanding tongue 60 which extends about the perimeter of the base portion and is closely receivable within a groove 62 formed in the base of membrane capture housing 40 (FIG. 5). When the ullage substrate and the membrane capture housing are assembled in the manner shown in FIG. 5, the periphery of distendable membrane assembly 34 will be securely clamped within groove 62 by tongue 60. After the parts are thus assembled, housing 40 is bonded to substrate 38 by any suitable means such as adhesive or sonic bonding. This done, cover 36 is mated with housing 40 in the manner shown in FIG. 5 and bonded in place. Cover 36 is preferably constructed from a substantially transparent plastic material which is impermeable to fluids, including gases.

The apparatus of this latest embodiment of the invention is adapted to be filled with the selected medicinal fluid either at time of manufacture or in the field as may be desired. Filling is accomplished by introducing fluid under pressure into inlet passageway 48 and thence into reservoir 46 via luer fitting 50. As the fluid under pressure flows into the reservoir, it will cause membrane assembly 34 to distend outwardly from protuberance 44 in the manner shown in FIG. 5. Luer fitting 50 includes a skirt portion 50a, a valve seat 50b and a biasing spring 50c (see also FIG. 22). Receivable into valve seat 50b is a ball check valve 50d which will lift from seat 50b against the urging of spring 50c during reservoir filling, but will sealably engage seat 50b after the reservoir has been filled. Inlet 48 is closed by a closure cap 51 prior to and following the filling step.

Figure 3A:
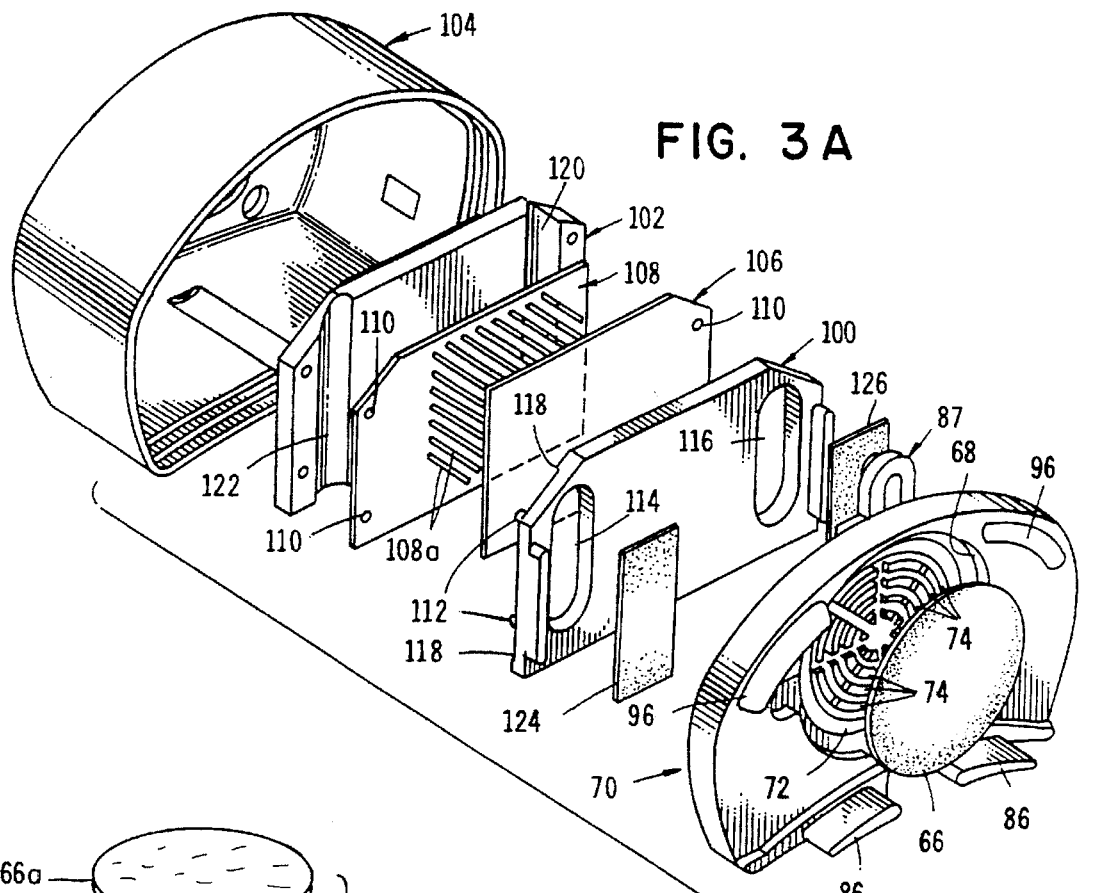
FIG. 3A is a generally perspective, exploded view of the downstream portion of one form of the fluid dispensing apparatus of the invention showing the flow indicator means and a portion of the flow control means.

While the stored energy means can be in the form of a single prestressed or unstressed isotropic, elastomeric distendable membrane, it is here shown as a laminate assemblage made up of a plurality of initially generally planar distendable elements or films. Referring particularly to FIG. 3C, the stored energy means can be seen to comprise a laminate assemblage 34 made up of individual layers 34a, 34b, 34c, and 34d. Assemblage 34, which is typically prestressed, functions in much the same way as the distendable membranes described in Ser. No. 08/046,438 and cooperates with ullage substrate 38 to define a fluid chamber, or reservoir 46. However, by constructing the stored energy means from a composite of distinct elements or layers, the elastic characteristics of the stored energy means can be precisely tailored in the manner described in Ser. No. 08/046,438.

As previously discussed, as the distendable membrane assemblage 34 is distended by the fluid pressure exerted by the fluid flowing into inlet 48, internal stresses are formed therein which continuously urge the assemblage toward engagement with protuberance 44 as it tends to return toward its original configuration. As the assemblage moves toward protuberance 44, fluid within reservoir 46 will be uniformly and controllably forced outwardly through longitudinally extending passageway 52 in protuberance 44 and then into passageways 54 and 56 of portion 38a of ullage substrate 38.

For certain applications it is desirable to provide on one or more layers of the membrane assemblage a surface which is specifically designed to be compatible with the fluid to be delivered. For example, layer 34e can be provided on its under-side with a compatibility layer 34f constructed from a co-polyester sold by DuPont under the name and style of HYTREL.

Reference should be made to U.S. Ser. No. 08/046,438 for the various materials that can be used to construct the base assembly, the cover and the membrane assemblage identified in the preceding paragraphs.

Turning next to a consideration of the flow rate control subassembly of this latest form of the invention, this subassembly includes novel flow control means which are disposed externally of reservoir 46 for controlling the rate of fluid flow of fluid from the device. In the embodiment of the invention shown in FIGS. 3A through 7, the flow control means comprises a rate control membrane 66 (FIG. 3A) which is closely received within a circular recess 68 formed in support means shown here as a membrane support structure 70. The downstream wall 72 of recess 68 is provided with fluid distribution means comprising a multiplicity of circumferentially spaced, manifolding stand-off elements 74 against which membrane 66 is held in engagement by a disc-like member 76 (FIG. 3B) which is receivable within recess 68 (see also FIGS. 16 and 17). As best seen by also referring to FIGS. 12 and 15, member 76 is provided with fluid collection means shown here as a multiplicity of circumferentially spaced, manifolding stand-offs 78 which engage membrane 66 when member 76 is in position within cavity 68. More particularly, as indicated in FIG. 14, when member 76 is in place within cavity 68, the flow control membrane 66 is bonded at its circumference to member 70 and is securely positioned between stand-offs 74 and 78 which cooperate to define a multiplicity of concentric and radial extending fluid passageways, which function to direct fluid flow through the flow control means. Air within chamber 69 is vented via vent patch 92a and opening 92b (FIG. 3B).

Figure 3D:
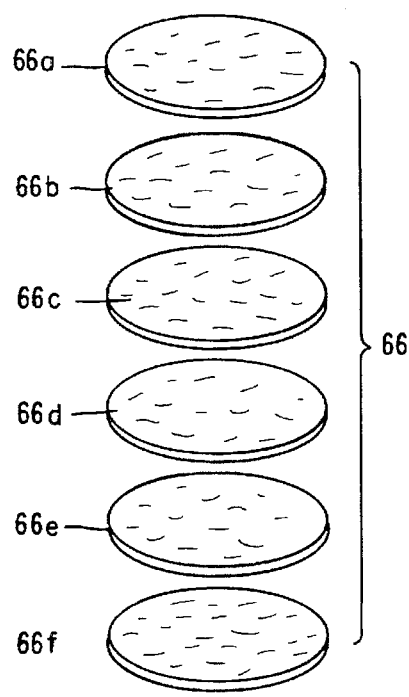
FIG. 3D is a generally perspective, exploded view of the fluid flow control assembly illustrating its laminate construction.
Figure 3C:
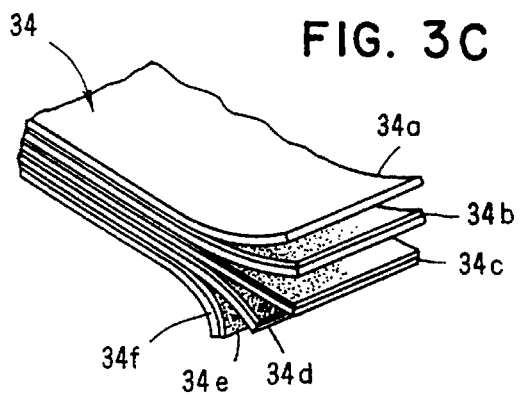
FIG. 3C is a generally perspective, fragmentary view of a portion of the distendable membrane assembly of the apparatus.
Figure 4:
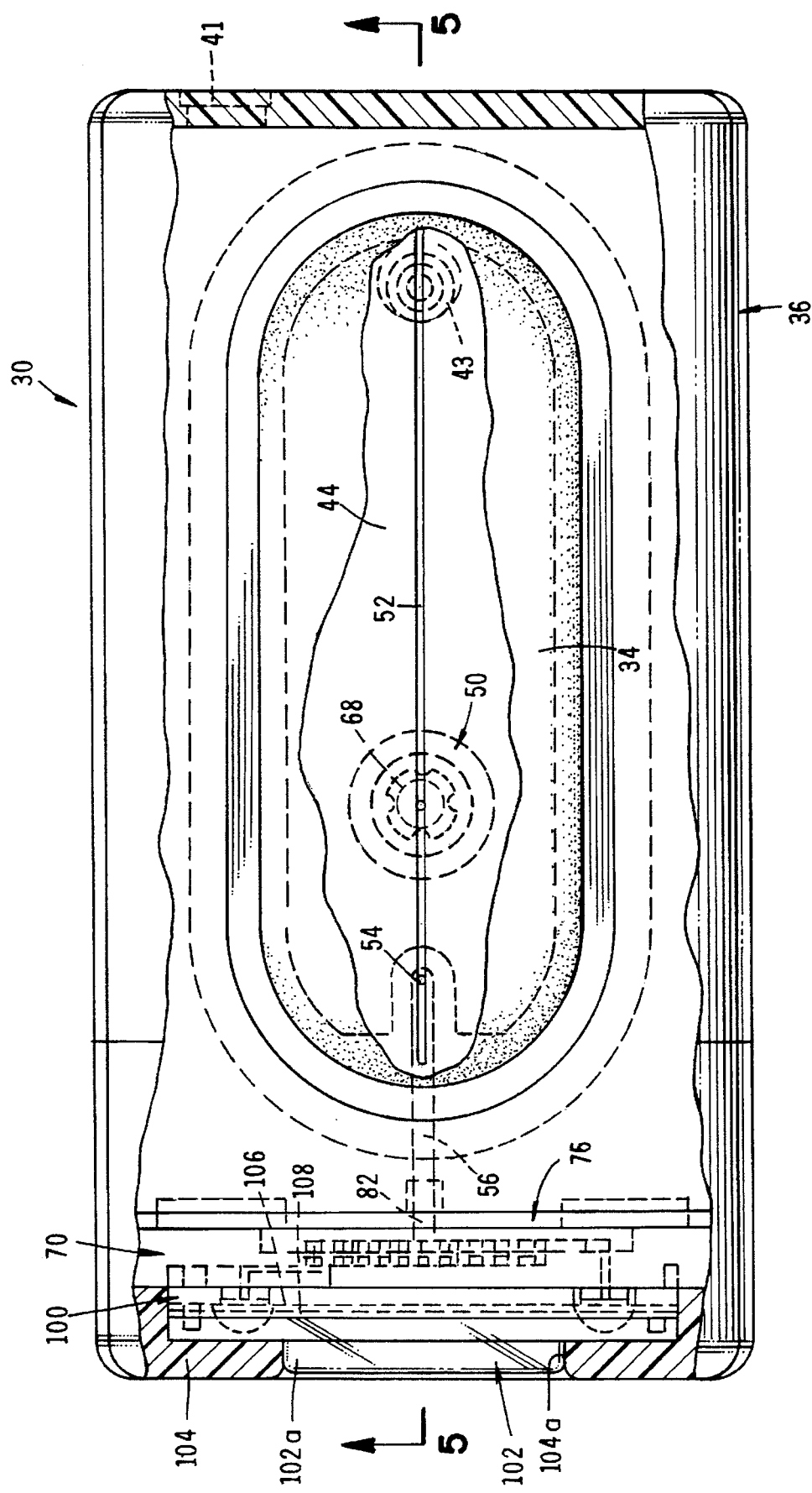
FIG. 4 is a top plan view of the apparatus, partly broken away to show internal construction.

As shown in FIG. 3D, flow control 66 here comprises a laminate construction made up of layers 66a, 66b, 66c, 66d, 66e, and 66f. More particularly, layer 66a comprises first filter for initially filtering the fluid, while layer 66b comprises a second filter for providing a second, more refined, filtering of the fluid. Layer 66c is here shown as a first flow rate control membrane for controlling flow at a first rate. Layer 66e is a second flow rate control membrane for controlling flow at a second rate. Disposed intermediate rate control membranes or layers 66c and 66e is a distribution means or porous distribution layer 66d for distributing the fluid flowing through membrane 66c across the surface of membrane 66e. Layer 66f comprises a porous support member for supporting membrane 66e.

First and second filters 66a and 66b can be constructed from polyether sulfone sold by Gelman Sciences under the name and style of SUPOR.

Flow rate control layers 66c and 66e can be constructed from a porous polycarbonate material available from Poretics Corporation or from Corning Costar Corporation. The distribution or separation layer can be constructed from polypropylene available from Gelman Sciences. It is preferable that the surface and orifice chemistry of each layer of the flow control 66 be rendered hydrophillic.

Figure 15:
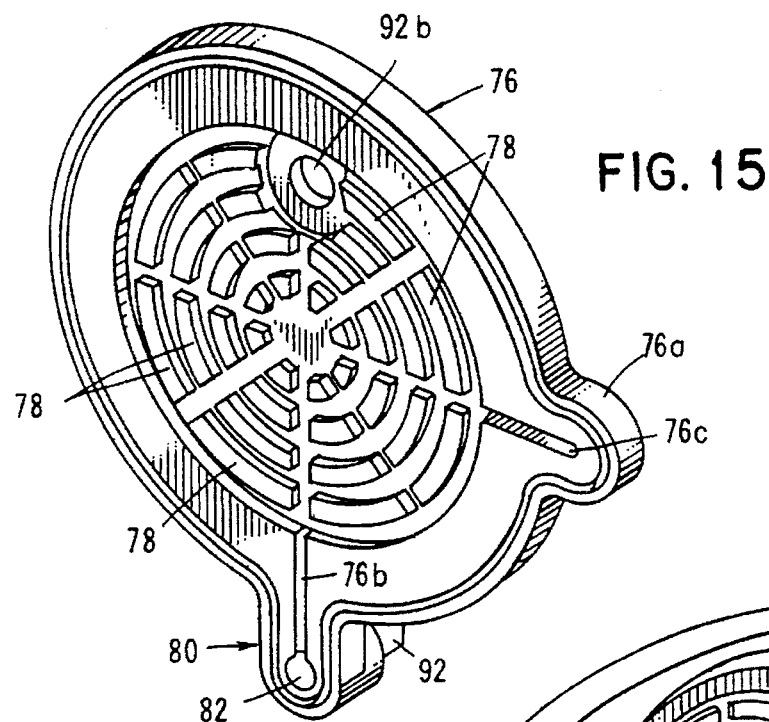
FIG. 15 is a generally perspective view of the cover for the rate control apparatus of the invention.
Figure 16:
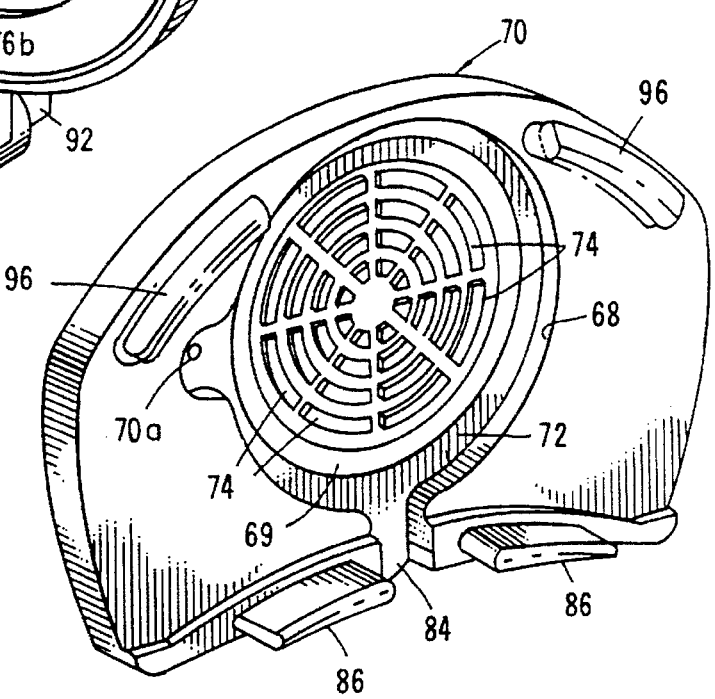
FIG. 16 is a generally perspective, front view of the substrate portion of the rate control apparatus.

As best seen in FIGS. 3B and 15, member 76 includes a downwardly extending fluid inlet leg or segment 80 which is provided with a fluid passageway 82. Passageway 82 is adapted to communicate with chamber 69 when member 76 is mated with support structure 70. As best seen in FIG. 16, support structure 70 has a centrally disposed recess 84 that receives inlet segment 80.

Formed on either side of recess 84 are wing-like protuberances 86 that are received within spaced-apart, arcuate-shaped cavities 88 formed in the base portion 38a of ullage substrate 38. Also formed in substrate 38 is a socket 91 (FIG. 7) which closely receives a tubular extension 92 formed as a part of inlet segment 80 (FIG. 14). Located proximate the upper edge of support structure 70 are spaced-apart capture grooves 96, which attach cover 36 to member 70.

As shown in FIG. 5, when the flow control subassembly is mated with the reservoir assembly, fluid inlet passageway 82 of member 76 is placed in fluid communication with reservoir 46 via passageways 54 and 56. With this construction, when fluid is forced through fluid passageway 52 of protuberance 44 by the stored energy means, the fluid will flow into passageway 54, next into passageway 56, then into passageway 82 of member 76, and finally into chamber 69 formed in member 70. As the fluid under pressure flows into the upstream portion of chamber 69 behind membrane 66, it will be distributed by stand-offs 78 so that it will uniformly flow through membrane 66 and toward the fluid outlet port of the flow control subassembly. As best seen in FIGS. 12 and 18, the outlet port comprises an assembly 87 which is receivable in a cavity 73 formed in the back of downstream wall 70d of substrate 70. Assembly 87 includes a fluid outlet 90 and an internal chamber 93, the purpose of which will presently be described. A flexible strain relief tube 91 is sealably receivable over the extremity of assembly 87 (FIG. 10) and a centrally disposed microbore delivery tube 95 is telescopically received internally of the extremity in the manner shown in FIG. 10. During filling of chamber 93, air therewithin can be vented to atmosphere via vent patch 92a.

The flow control means can also comprise an assemblage of a plurality of layers of permeable materials, P-1, P-2, and P-3 of the character seen in FIG. 31 of U.S. Pat. No. 5,205,820. These layers, which may be composites, thin films, or porous substrates, may be constructed of any one of the materials described in U.S. Pat. No. 5,205,820 so that the fluid pressure flow characteristics of the assemblage can be precisely tailored for the particular medicinal or other fluid being dispensed. Reference should be made to U.S. Pat. No. 5,205,820 for a further description of the construction and operation of the flow control membrane.

Considering now the flow indicator means of the invention, this novel means visually distinguishes among three conditions of operation, namely normal fluid flow, fluid flow blockage or occlusion, and reservoir empty. Turning to FIG. 3A, the flow indicator means here comprises an indicator base or platform 100, a support or lens plate 102, and a hollow housing 104 within which the platform and the support plate are mounted. As seen in FIG. 12, plate 102 has a viewing lens 102a which indexes with an aperture 104a provided in housing 104.

Disposed between platform 100 and plate 102 are first and second indicia-carrying means shown here as thin films.

These films identified here as 106 and 108, are in intimate contact and are constructed from a substantially transparent, flexible polymer material such as mylar. The indicia-carrying means need not be thin films, but rather can be any type of surface presenting member upon which indicia can be provided. The downstream surface of the inferior or first film 106 is printed with three integrated symbols 107 (FIG. 23), namely, a blue circle 107a (FIG. 25), a green arrow 107b (FIG. 27), and a red X 107c (FIG. 29), each consisting of diagonal stripes of color printed in an alternating pattern (blue, green, red, blue, green red, and so on. (FIGS. 23 through 29)). The superior, or second film 108 serves as a "mask" over the inferior film 106 and is printed with a pattern of diagonal alternating clear and opaque strips 108a that occur in a 1:2 ratio. The printed ratio of the superior "mask" allows only one colored symbol to appear at a time when viewed through viewing lens 102a in plate 102. The inferior and superior films are provided at their opposite ends with apertures 110 which receive retention pins 112 provided on platform 100 (FIG. 12) which permit attachment of the film to platform 100 in a manner such that the non-patterned portions of each film covers actuator slots 114 and 116 provided proximate each end of platform 100 with the patterned portions of both the superior and inferior films being maintained in the index. With this construction, each thin film is able to move in opposing directions parallel to the film plane with its range of motion limited to one axis in the film plane by edge guides 118 provided on platform 100 (FIG. 12). As the films move, the visible symbol pattern changes due to the transverse displacement of the patterns imprinted thereon.

Referring particularly to FIGS. 3A, 9 and 14, it can be seen that support plate 102 is provided with transversely spaced, channel-like depressions 120 and 122 which index with slots 114 and 116 respectively when the components are assembled in the manner shown in FIGS. 9 and 14. Aligned with the up-stream side of slots 114 and 116 are mechanical actuator means, here provided as mechanical actuators or elastomeric elements 124 and 126. More particularly the first actuator element 124 aligns with slot 114 and the second actuator element 126 aligns with slot 116.

In a manner presently to be described, the mechanical actuator means are deflected from their initial configuration whenever there is sufficient fluid pressure present within the fluid flow path to cause their outward deflection toward thin films 106 and 108. During operation the first mechanical actuator element 124 is deflected by fluid pressure of reservoir 46. More particularly, when there is sufficient fluid pressure in the fluid reservoir and fluid is being delivered by the stored energy means of the device, the first mechanical actuator means is deflected outwardly so as to urge the non-patterned portion 109 of indicator film 108 into expansion channel 122. As the film arches into channel 122, the printed portion of the film is transversely displaced a specific distance. This film displacement re-aligns the printed symbol patterns on the inferior film 106 with the mask pattern on the superior film 108 and results in a change of the symbol (in this case an arrow) that is visible through the support plate view aperture 102a (see FIGS. 1, 26 and 27).

Figure 28:
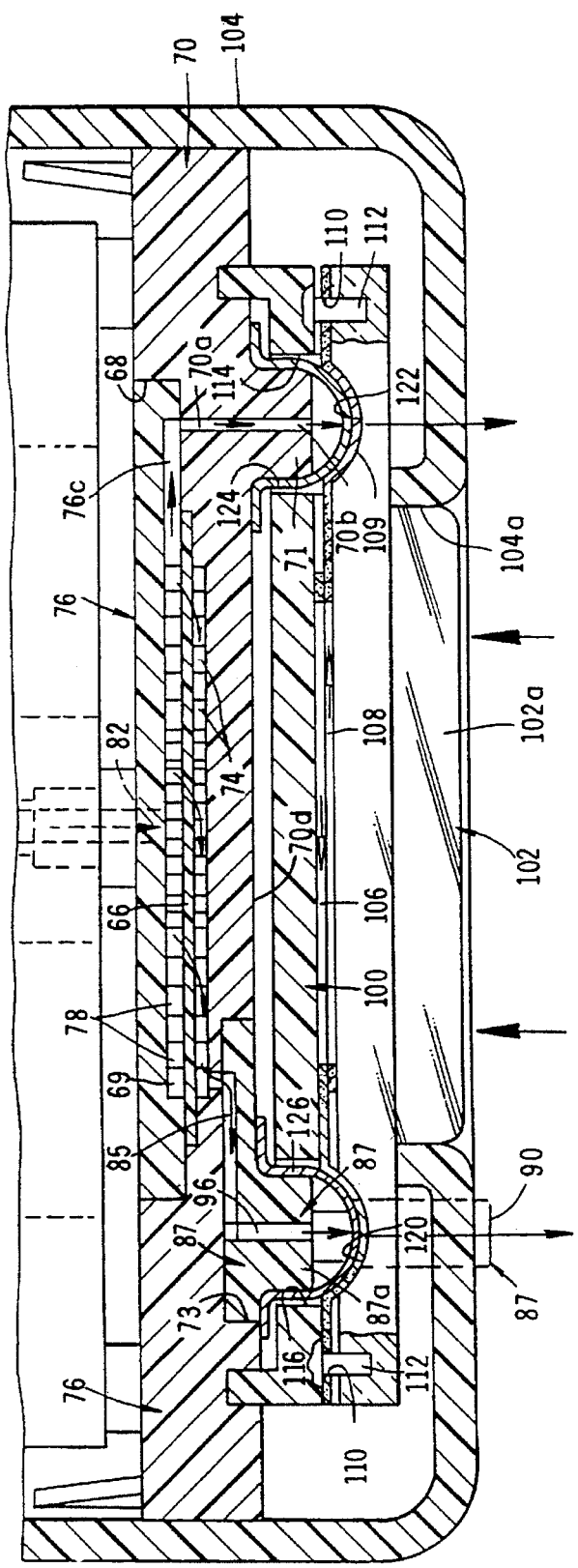
FIG. 28 is a cross-sectional view similar to FIG. 24, but showing the indicator means as it appears when there is a blockage downstream of the indicator means that prevents normal fluid flow.
Figure 29:
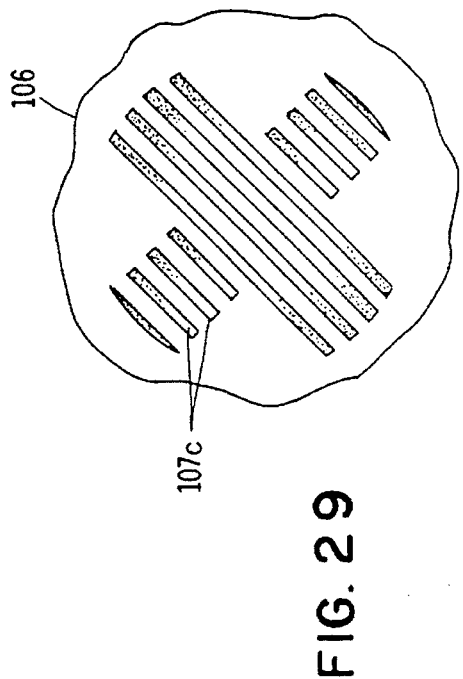
FIG. 29 is a fragmentary plan view of the symbol that is viewable by the user when the apparatus is in the configuration shown in FIG. 28.

As can be observed by referring to FIGS. 28 and 29, both the first and second mechanical elastomeric actuator elements 124 and 126 are inflated and deflected outwardly toward their respective extension channels when the device is filled and primed but not in a state of delivery or when there is a build up of fluid pressure during delivery that is caused by blockage of the delivery line downstream from second mechanical actuator element 126. While element 124 can be deflected by normal line pressure, element 126 is deflected only by pressure buildup resulting from the downstream blockage. When both mechanical actuators are deflected outwardly, both the superior and inferior films are displaced transversely to a second position revealing a second symbol, as for example, an X as viewed through the viewing aperture of the support plate (see FIGS. 28 and 29).

A third alignment of symbol patterns as shown in FIGS. 24 and 25 is visible when the device is in an unfilled state or when the delivery line is open, the reservoir is empty and fluid delivery to the patient has been completed. In this case, there is no fluid pressure in the line on either the upstream or downstream side of the flow control means and thus both the first and second mechanical actuator elements are in a non-deflected position. In this condition, the inferior and superior films are not transversely displaced and thus exhibit a third combination of patterns resulting in a third symbol as, for example, a circle being visible through the viewing aperture of the support plate (see FIG. 25). Actuating elements 124 and 126 can be precisely tailored to deflect under various pressures thereby permitting great apparatus versatility.

In considering the method of operation of the device and the manner in which fluid flows through the device, reference should be made particularly to FIGS. 5, 10, and 12. During the filling step, the fluid to be dispensed is introduced into reservoir 46 via a fluid inlet conduit 49a (FIG. 1) which is connected to luer fitting 50. Fluid flowing into the fitting lifts check valve ball 50d against the urging of spring 50c and causes the distendable membrane assembly to be displaced away from ullage protuberance 44 in the manner shown in FIG. 5. Air within housing 40 and cover 36 will be suitably vented to atmosphere via a vent 41 which is receivable within a vent aperture 41a provided in housing 40 (FIG. 3B). During the filling step, the gaseous component of the fluid is vented to atmosphere via a vent patch 43 provided in portion 38a of substrate 38 (FIGS. 3B and 5).

Figure 17:
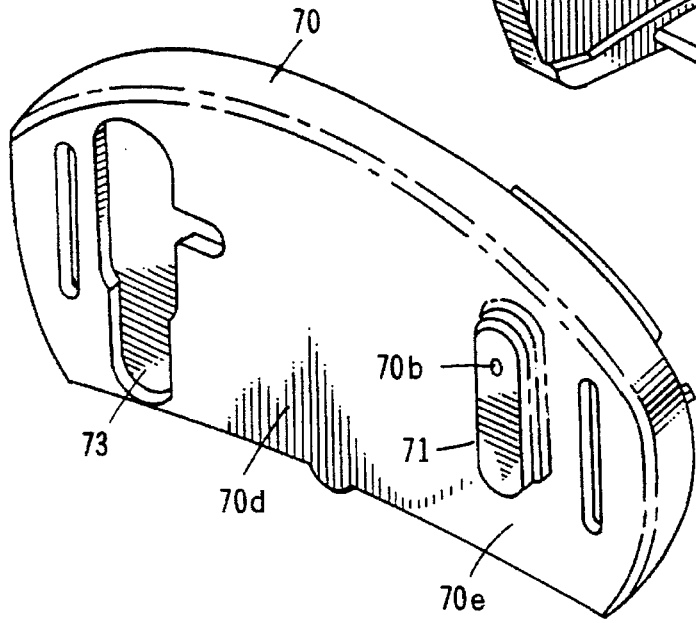
FIG. 17 is a generally perspective rear view of the substrate portion.
Figure 26:
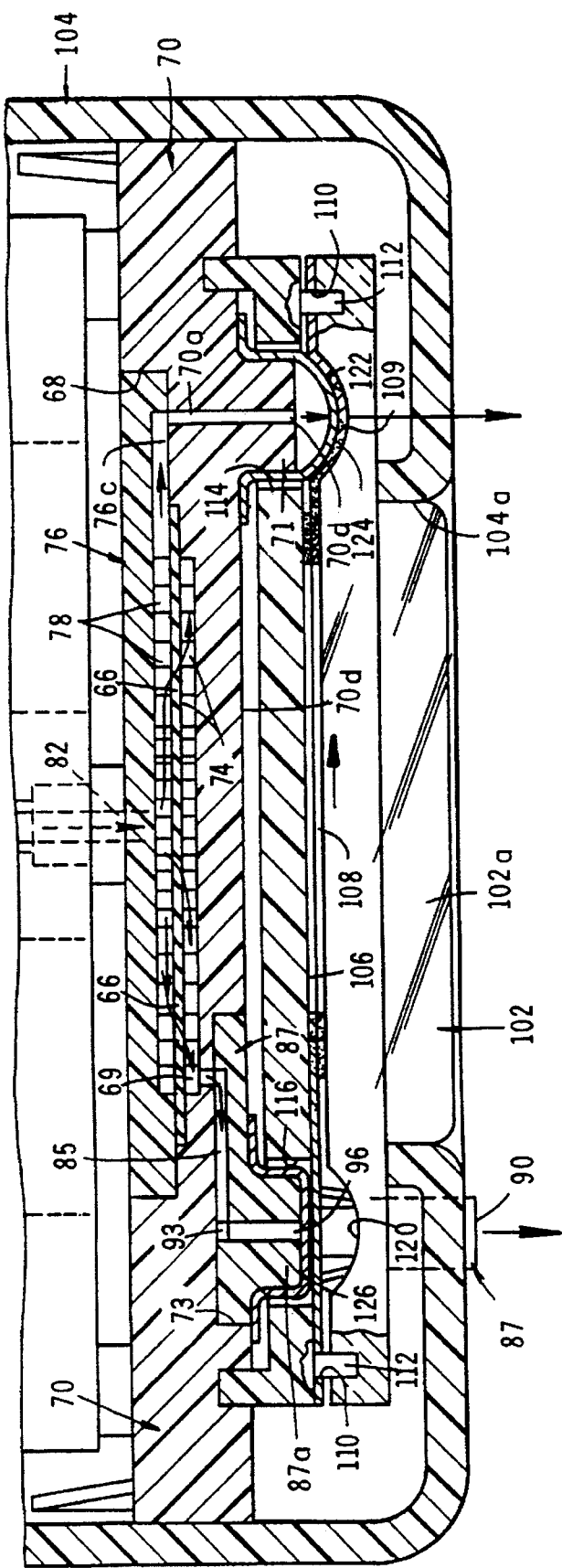
FIG. 26 is a cross-sectional view similar to FIG. 24 but showing the indicator means as it appears when fluid is flowing through the apparatus in a normal fashion.
Figure 27:
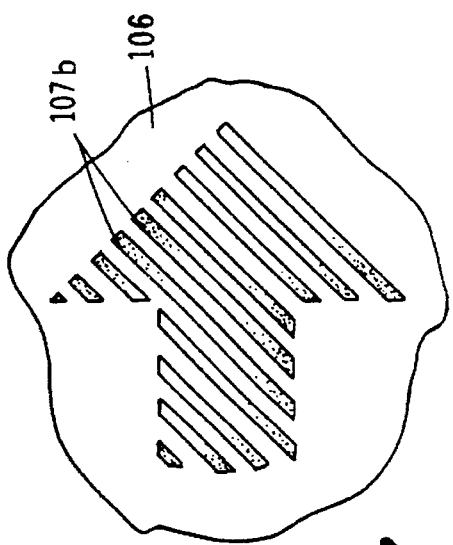
FIG. 27 is a fragmentary plan view of the symbol that is viewable by the user when the apparatus is in the configuration shown in FIG. 26.

During the fluid dispensing step, the prestressed membrane assembly will tend to return toward a less distended configuration causing fluid within the reservoir to flow outwardly of passageway 52 and into passageways 54 and 56. The fluid under pressure will next flow into passageway 82 of disc-shaped member 76. Turning particularly to FIGS. 15 and 16, it is to be observed that a portion of the fluid entering chamber 69 of member 70 from passageway 82 and upstream of membrane 66 can by pass flow rate control member 66 and flow directly toward an ear-shaped extension 76a provided on member 76 via flow passageways 76b and 76c. From passageway 76c, the fluid will flow under pressure into a passageway 70a formed in substrate 70 and toward passageway outlet 70b. Referring also to FIG. 17, it is to be noted that passageway 70a extends through a protuberance 71 formed on end wall 70c of substrate 70. This construction permits the fluid flowing into ear-shaped protuberance 76a to flow through passageway 70a and impinge directly upon flow indicator element 124 which sealably engages the protuberance, causing it to deform outwardly in a manner to force portion 109 of indicator film 108 to arch into expansion channel 122 (FIG. 26). This, in turn, will cause transverse displacement of indicator film 108 in the manner previously described.

As indicated in FIG. 28, fluid flowing through passageway 82 of disc-shaped member 76 will also be distributed over the upstream face of the rate control membrane 66 by the fluid distribution means, or protuberances 78 and will pass through the membrane at a predetermined controlled rate. The fluid flowing through the rate control membrane will be collected by the fluid collection means or protuberance 74 and then will flow via passageway 85 into passageway 93 of outlet port assembly 87. The fluid will then flow outwardly of the device through fluid outlet 90 to which an infusion line 93 is connected. (FIGS. 1, 18, 19, and 20). It is to be observed that a portion of the fluid flowing into outlet port assembly 87 is free to flow through a passageway 96 provided in a protruding portion 87a thereof. If there is a blockage which prevents continued free fluid flow outwardly of the device through outlet 90 and infusion line 95, fluid, under pressure, F-2 will impinge upon indicator element 126 causing it to deflect outwardly in the manner shown in FIG. 28. This outward deflection of element 126 will urge a portion of indicator film 106 into receiving channel 126 of the lens plate causing transverse movement of film 106 so as to reposition film 106 relative to film 108. Should fluid flow into chamber 92 cease, indicator element 126 will return to its at-rest position as will film 106. Similarly, if fluid flow from the reservoir ceases, film 108 will also return to its at rest position thereby once again causing the "O" symbol to be viewable through the viewing lens.

The method of the invention for constructing a fluid delivery device of the character described in the preceding paragraphs will now be described. Referring to FIG. 30, one type of apparatus for accomplishing the first step of one form of the method of the invention is there diagrammatically illustrated. This initial step of the method comprises simultaneous stretching the elastomeric membrane substantially uniformly, differentially, uniaxially, or biaxially using a stretching means of the general character shown in FIG. 30. This membrane stretching means here comprises a stretching, or elongation fixture 150 which functions to controllably stretch the elastomeric membrane 34 in the manner shown in FIG. 30. Stretching fixture 150 includes four circumferentially spaced membrane gripping assemblies 154, each having gripping elements 156 for gripping the edges of the elastomeric, isotropic membrane 34. Each of the gripping assemblies 154 is affixed to a slide block 158 which is slidably movable along a pair of tracks 160 by means of a screw assembly 162 which is carried by an end plate 160a provided on tracks 160. Each screw assembly 162 comprises a threaded rod 162a, one end of which is connected to a slide block 158. As the threaded rod is rotated by means of a handle 162b, the slide block, along with its associated gripping element 156, will move outwardly relative to the center of membrane 34 causing it to extend outwardly. A manual vernier 166 is provided on each screw assembly for indicating the extent of movement of the slide block relative to the membrane.

Figure 30A:
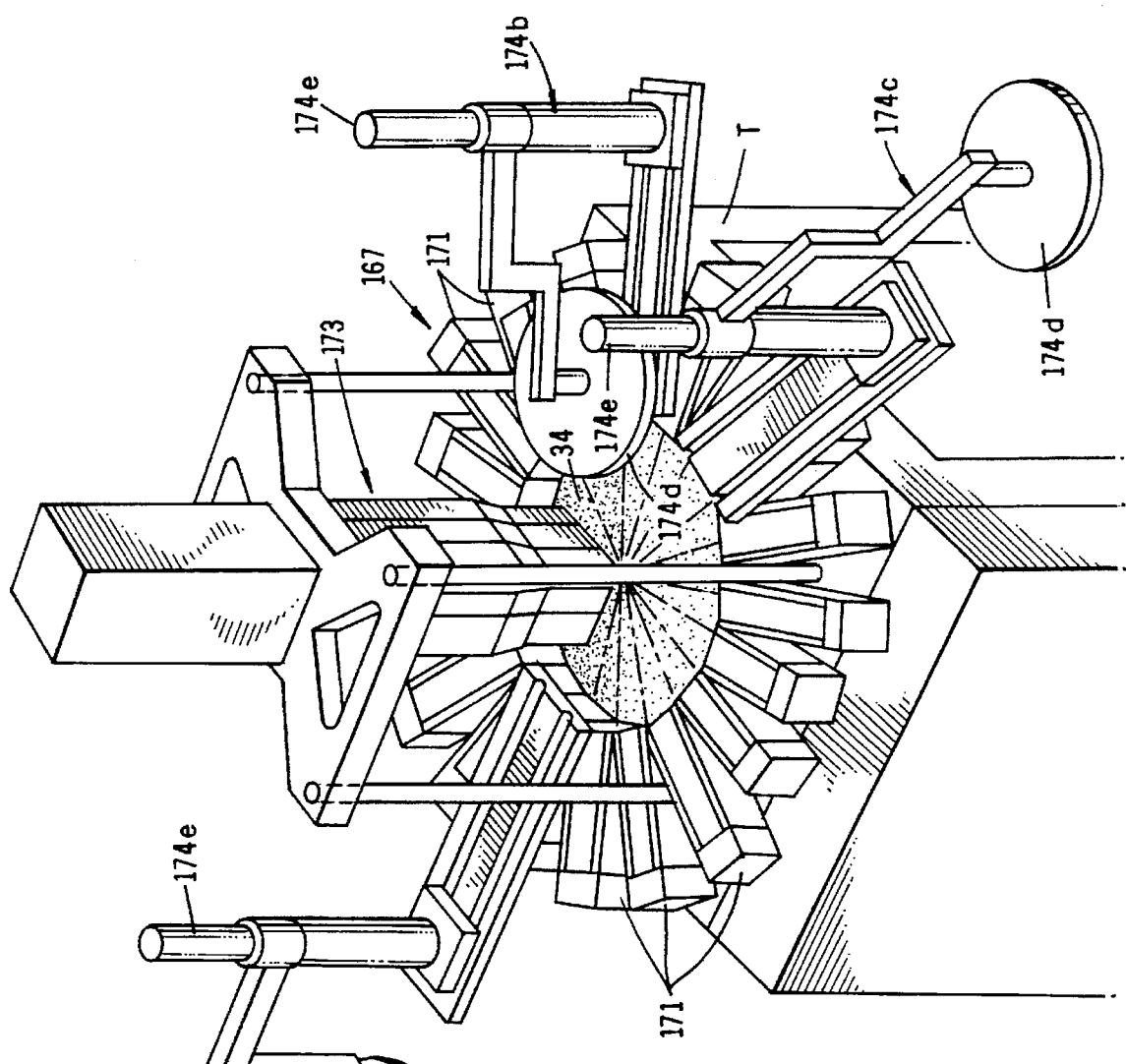
FIG. 30A is a generally perspective view of another type of apparatus used in accomplishing the method of the invention.
Figure 30B:
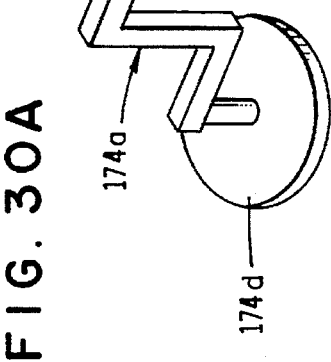
FIG. 30B is a fragmentary, cross-sectional view of one of the membrane gripping elements of the apparatus of FIG. 30A.

Turning to FIG. 30A, another type of apparatus usable in carrying out the method of the invention is there illustrated. This apparatus also includes a membrane stretching fixture 167 which functions to controllably radially stretch the elastomeric membrane 34 in the manner illustrated in FIG. 30a. Stretching fixture 167 includes a plurality of circumferentially spaced mechanically actuated membrane gripping assemblies 171, each having gripping elements 171a (FIG. 30B) for gripping the edges of the isotropic membrane. Each of the gripping assemblies 171 is mounted on a support table "T", which also supports the mechanical equipment for operating assemblies 171. This type of equipment is of a character well known to those skilled in the art. As the gripping assemblies are actuated, the gripping elements will move radially outwardly relative to the center of membrane 34 causing it to extend outwardly a predetermined amount.

Also forming a part of the apparatus of FIG. 30A is a centrally disposed sonic welding apparatus 173, the purpose of which will presently be described. Surrounding the sonic welder are vacuum operated article pick-up devices 174a, 174b, and 174c which can be used to position the cover portion of the fluid delivery devices relative to the membrane during the assembly operation. Each of these pick-up devices includes a gripping member 174d which is rotatable about a support shaft 174e.

Referring next to FIG. 31, following prestressing of membrane 34, using either the fixture shown in FIG. 30 or the fixture shown in FIG. 30A, the next step in the method of the invention comprises affixing the prestressed membrane 34 to the periphery of the base portion 38a of ullage substrate 38. This is accomplished by moving capture housing 40 downwardly relative to base portion 38a in a manner such that prestressed membrane 34 will be securely clamped between the peripheral portions of base 38a and the peripheral portion of capture housing 40. As the capture housing is moved toward the base, which is typically supported beneath membrane 34, the membrane will engage and conform to the ullage defining means or protuberance 44 in the manner illustrated in FIG. 31 (see also FIG. 3B).

As previously discussed herein, capture housing 40, as well as membrane 34, can be interconnected with base portion 38a in any suitable manner well known to those skilled in the art, such as adhesive or sonic bonding. In the embodiment of the invention shown in FIGS. 30 and 31, base portion 38a is provided with a capture groove 59 and an adjacent tongue 60. Capture housing 40, on the other hand, is provided with a capture tongue 61 and a groove 62 which closely receives tongue 60 as the capture housing moves into engagement with base portion 38a in the manner shown in FIGS. 5, 6, and 31.

Base portion 38a is also provided with an upstanding membrane cutting means or protuberance 155 which circumscribes tongue 60 and functions to cleanly cut membrane 34 upon capture housing 40 engaging base portion 38a. Protuberance 155 also uniquely functions as an energy director for sonic weldment of housing 40 to base 38a. Simultaneously with the cutting of the membrane, the capture housing can be sonically welded to the base portion in the proximity of protuberance 155 through use of a sonic welder 173 (FIG. 30A) by techniques well understood by those skilled in the art. After the sonic welding step, the capture plate and membrane are securely, sealably interconnected with the base portion. Manipulation of the capture housing can be accomplished using the pick-up devices shown in FIG. 30A when this type of fixture is used.

Turning now to FIG. 32, the next sequential steps in the practice of the method of the invention are there illustrated. More particularly, after interconnection of the membrane and the housing with base portion 38a to form a base assembly 175, cover 36 is connected to base assembly 175 to form a fluid delivery reservoir assembly 177 of the character depicted in FIG. 32. Cover 36 can be interconnected with base assembly 175 by any suitable means such as adhesive bonding or sonic welding.

The next step in the present form of the method of the invention is to connect support structure 70 of the rate control assembly of the invention with fluid delivery reservoir assembly 177. This step is accomplished in the manner previously described herein by inserting wings 86 of support 70 into the wing-receiving apertures 88 formed in base portion 38a. Following insertion of wings 86 into apertures or sockets 88 (FIG. 7), wings 86 are secured in place by any suitable bonding means such as adhesive bonding or sonic welding to form the controlled fluid delivery subassembly 179 (FIG. 32).

This done, the final step in this form of the method of the invention comprises interconnecting housing 104 of the indicator assembly 181 with the control delivery assembly 179.

Figure 33:
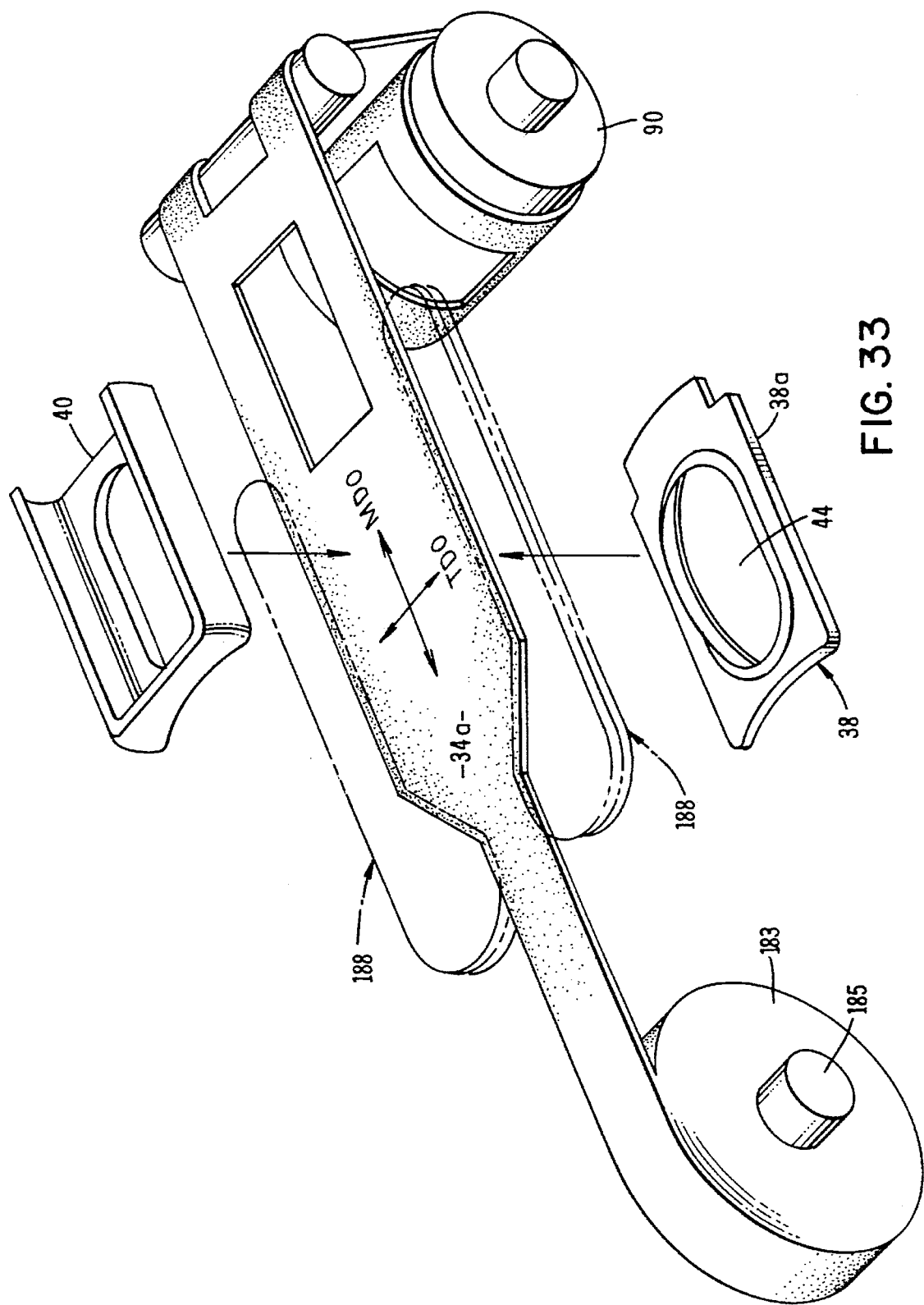
FIG. 33 is a generally perspective exploded view of an apparatus for carrying out the first step of an alternate form of the method of the invention.

Turning now to FIG. 33, another novel form of the method of the present invention is there diagrammatically illustrated. In accordance with this continuous assembly type method of the invention, the elastomeric membrane, which is to be interconnected with base 38a, comprises a length of elastomeric membrane 34a that is controllably removed from a first roll 183. Roll 183 comprises a long length of elastomeric membrane material that has been wound upon a spindle 185 which is suitably mounted for rotation about its transverse axis so that the membrane material can be controllably unrolled therefrom.

After a length of elastomeric membrane is removed from roll 183, it is interconnected with a series of longitudinally spaced clamps or grippers 187 (FIGS. 34 and 34A) which comprise a part of a simultaneous biaxial stretching means which is used to controllably prestress the membrane. The biaxial stretching means can take several forms, but preferably comprises a tenter apparatus 188 of the general character illustrated in FIG. 34. While a number of different types of tenter apparatus have been suggested in the past and their design and operation is well known to those skilled in the art, a tenter apparatus of the general character described in German patent 1,504,479 issued to Erwin Kampf can be used in modified form to accomplish the biaxial stretching step of the invention.

Figure 34:
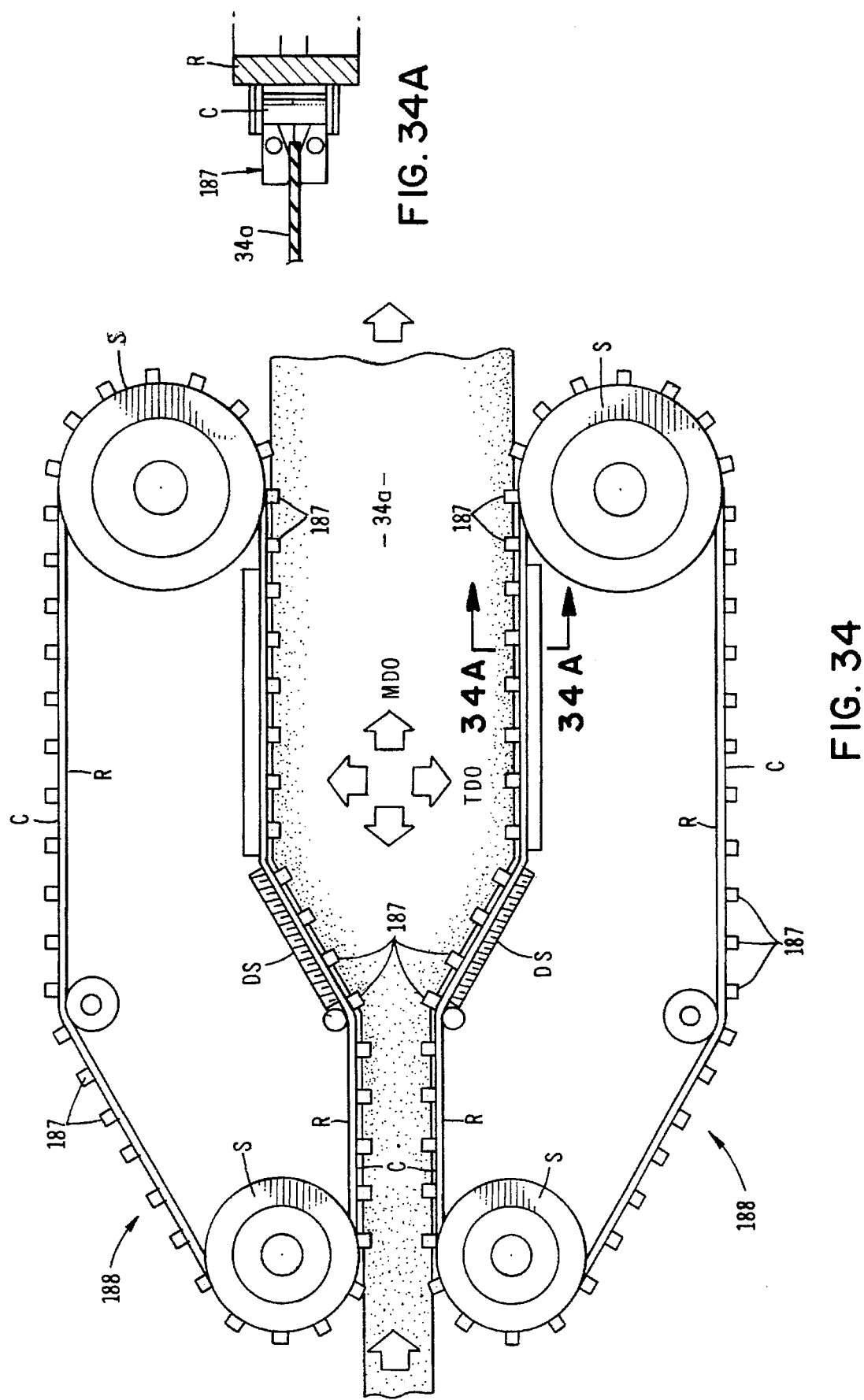
FIG. 34 is a top plan diagrammatic view of a portion of the apparatus depicted generally in FIG. 33 showing the tenter frame apparatus of the invention.

As best seen in FIG. 34, as the membrane is unrolled from roll 183, it is introduced into the tenter apparatus 188 in a manner such that the edges of the membrane are gripped by gripping clamps 187. These gripping clamps are, in turn, operably associated with elongated endless chain assemblies "C" and with guide rails "R" (FIGS. 34 and 34A), so that as the chains move about rotating sprockets "S" and differential screws "DS", the clamps diverge so as to controllably impart biaxial stretching forces to the membrane causing it to be stretched in the manner illustrated in FIGS. 33 and 34. Stretching is accomplished simultaneously in the machine direction orientation (MDO) and in the transverse direction orientation (TDO). It is to be understood that the stretching ratios can be precisely tailored to each axis to provide the desired initial strain energy density and extension pattern of the distendable membrane. Under certain circumstances, the extension values for the MDO axis may be different than the extension values for the TDO axis. It is to be appreciated, however, that in the same instances, no prestretch of the membrane will be desired and the tenter frame apparatus will not be used.

After the distendable membrane has been appropriately stretched to produce a prestressed membrane 34a of the desired biaxial dimension (FIG. 33), it is positioned over the upper surface of base portion 38a. This done, capture housing 40 is placed over membrane 34a and base portion 38a in a manner to urge a peripheral portion of the prestressed membrane into engagement with base 38a. Next, the prestressed membrane is cut and then, along with capture housing 40, is affixed to base 38a by any suitable bonding technique such as mechanical or adhesive bonding or sonic welding. Following the cutting step the remaining elastomeric membrane material is wound about a take-up drum 190 in the manner shown in FIG. 33 for later salvage. It is to be understood that the prestressed membrane can be of considerable width so that a plurality of side-by-side housings 40 can be placed over the membrane simultaneously and the membrane can then be cut at a plurality of side-by-side locations. The housings and the cut membranes can then be simultaneously joined with a plurality of bases 38a disposed in a side-by-side relationship beneath the membrane.

After membrane 34a and capture housing 40 have been affixed to base 38a to form base assembly 175 (FIG. 32), the next sequential steps in the device assembly are accomplished in the manner illustrated in FIG. 32 and as previously described herein in connection with the earlier described method of the invention.

Figure 35:
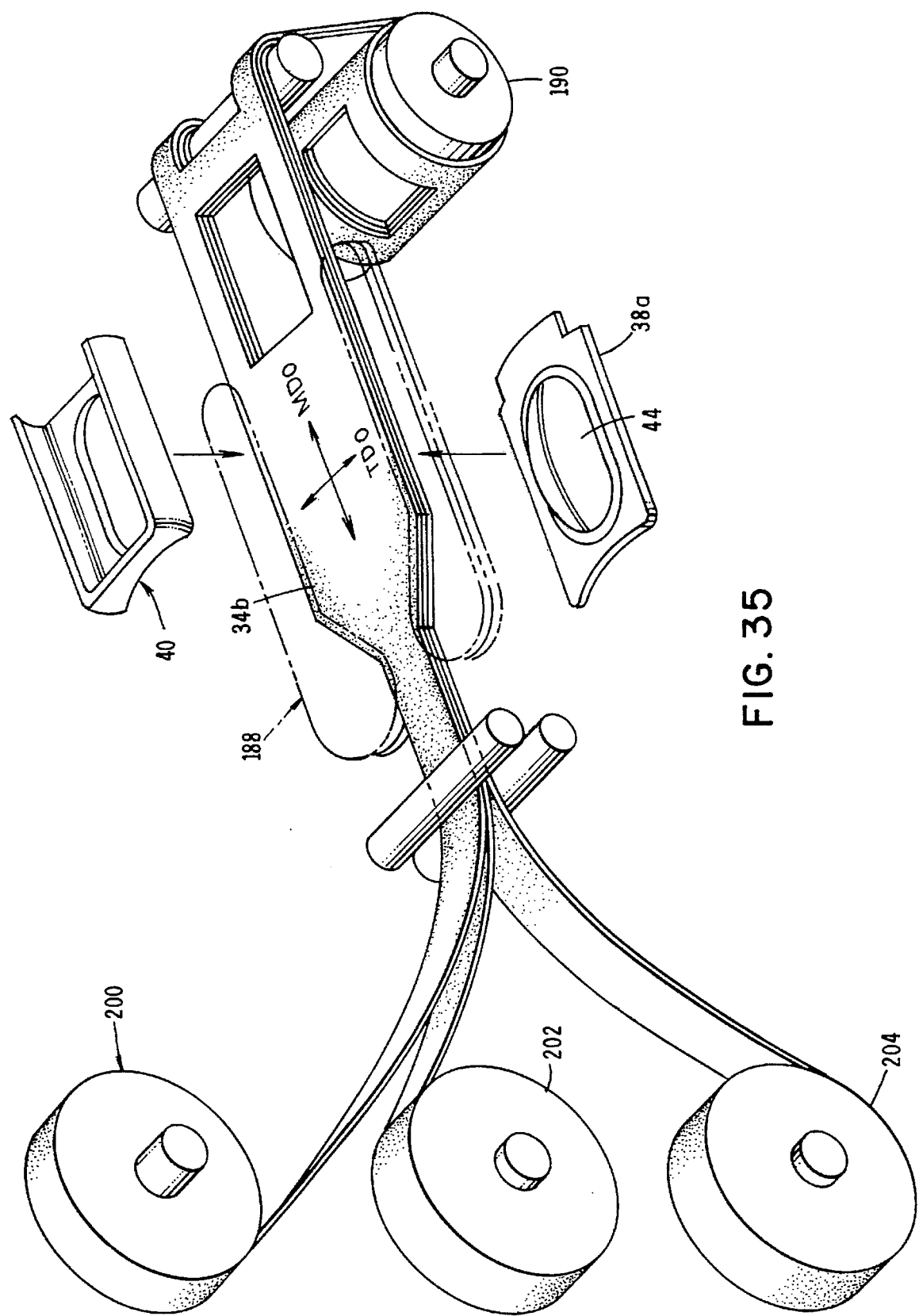
FIG. 35 is a generally perspective, exploded view of yet another type of apparatus for carrying out still another form of the method of the invention wherein an elastomeric laminate is formed, which laminate provides the stored energy for expelling fluids from the device.

Referring finally to FIG. 35, yet another novel form of the method of the present invention is there diagrammatically illustrated. In accordance with this continuous assembly type method of the invention, the stored energy source, which is to be interconnected with the base 38a, comprises a length of elastomeric laminate 34b that is formed by controllably removing lengths of membrane material from three rolls of material. These rolls, designated as 200, 202, and 204, each comprise a long length of elastomeric membrane material that has been wound upon a spindle which is suitably mounted for rotation about its transverse axis so that the membrane material can be controllably unrolled-from each of the rolls.

After a length of elastomeric membrane is removed from each of the rolls 200, 202, and 204, the lengths are brought into contact to form a laminate construction 34b. This laminate construction is then interconnected with a series of longitudinally spaced clamps 187 (FIG. 34) which comprise a part of the previously described biaxial stretching means which is used to controllably prestress the membrane. As before, the biaxial stretching means can take several forms, but preferably comprises a tenter apparatus 188 of the general character illustrated in FIG. 34.

As the membrane laminate 34b is formed in the manner shown in FIG. 35, it is introduced into the tenter apparatus 188 so that the edges of the laminate are gripped by gripping clamps 187. As shown in FIG. 34, these gripping clamps are, in turn, associated with elongated endless chain assemblies "C" and guide rails "R" so that as the chains move about rotating sprockets "S", and differential screws "DS", the clamps diverge so as to controllably impart biaxial stretching forces on the laminate causing it to be controllably biaxially stretched.

After the distendable elastomeric membrane laminate has been appropriately stretched to produce the prestressed laminate 34b the laminate is positioned over the upper surface of base portion 38a. This done, capture housing 40 is placed over the laminate and base portion 38a in a manner to urge a peripheral portion of the laminate into engagement with base 38a. Next the laminate is cut and then, along with capture housing 40, is affixed to base 38a in the manner previously described. Following the cutting step, the remaining elastomeric membrane laminate material is wound about a take-up drum 190 for later salvage.

After laminate 34b and capture housing 40 have been affixed to base 38a to form base reservoir assembly 175 (FIG. 32), the next sequential steps in the device assembly are accomplished in the manner illustrated in FIG. 32 and as previously described herein in connection with the earlier described embodiment of the invention.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A method of making a device for infusing medicinal fluid into a patient at a controlled rate, said device having a base provided with an upper surface including a central portion and a peripheral portion circumscribing the central portion, ullage-defining means disposed above said base, a distendable, elastomeric membrane superimposed over the base, a housing engageable with the base, and a cover covering the housing, the method comprising the steps of:

(a) gripping a peripheral portion of the distendable membrane in a manner to differentially stretch the membrane to produce a prestressed membrane;
   (b) subsequent to stretching the membrane placing the prestressed membrane over the ullage-defining means and the upper surface of the base;
   (c) emplacing the housing over the base and the prestressed membrane; and
   (d) sealably connecting the prestressed membrane and the housing to the base.

2. A method as defined in claim 1 in which the membrane is stretched biaxially.

3. A method as defined in claim 1 including the further step of capturing and then cutting the prestressed membrane as the housing is emplaced over the base.

4. A method as defined in claim 3 including sealably bonding the housing to the peripheral portion of the upper surface of the base.

5. A method as defined in claim 4 in which the housing is sonically bonded to the peripheral portion of the upper surface of the base.

6. A method as defined in claim 4 in which said device includes a cover covering the housing and in which the method includes the further step of connecting the cover to the housing.

7. A method of making a fluid delivery device for use in infusing medicinal fluid into a patient at a controlled rate having a generally plate like base provided with a fluid outlet and an upper surface including a central portion, a distendable elastomeric membrane superimposed over the base, a housing engageable with the base, one of said housing and said base having a groove and the other one a tongue receivable within said groove, a fluid rate control assembly for controlling fluid flowing from the fluid outlet of the base, a fluid flow indicator assembly for indicating fluid flow from the fluid outlet, and a cover covering the housing, the method comprising the steps of:

(a) stretching the distendable membrane to produce a prestressed membrane;
   (b) subsequent to stretching the membrane placing the prestressed membrane over the upper surface of the base;
   (c) emplacing the housing over the base and the prestressed membrane such that the membrane is clamped between the tongue and the groove;
   (d) cutting the prestressed membrane at a location proximate the tongue to provide a cut, prestressed membrane;
   (e) sealably interconnecting the cut prestressed membrane and the housing with the upper surface of the base to form a base assembly;
   (f) connecting the cover to said base assembly to form a fluid delivery assembly;
   (g) connecting the flow rate control assembly to the fluid delivery assembly to form a controlled delivery assembly; and
   (h) connecting the fluid flow indicator assembly to the controlled delivery assembly.

8. A method of making a device for infusing medicinal fluid into a patient at a controlled rate, said device having a base provided with an upper surface including a central portion, a distendable, elastomeric membrane superimposed over the base, and a housing engageable with the base, the method comprising the steps of:

(a) removing a first length of elastomeric membrane from a first roll of elastomeric membrane;
   (b) stretching said first length of distendable membrane to produce a first prestressed membrane;
   (c) removing a second length of elastomeric membrane from a second roll of elastomeric membrane;
   (d) stretching said second length of distendable membrane to produce a second prestressed membrane;
   (e) placing the said second prestressed membrane over said first prestressed membrane;
   (f) placing the first and second prestressed membranes over the upper surface of the base;
   (g) emplacing the housing over the base and the first and second prestressed membranes; and
   (h) sealably connecting the first and second prestressed membranes and the housing to the base.

9. A method as defined in claim 8 including the further step of removing a third length of elastomeric membrane from a third roll of elastomeric membrane including:

(a) stretching said third length of distendable membrane to produce a third prestressed membrane; and
   (b) placing the said third prestressed membrane over said second prestressed membrane.

10. A method of making a device for infusing medicinal fluid into a patient at a controlled rate, said device having a base provided with an upper surface including a central portion, a distendable, elastomeric membrane superimposed over the base, and a housing engageable with the base, the method comprising the steps of:

(a) removing a first length of elastomeric membrane from a first roll of elastomeric membrane;
    (b) removing a second length of elastomeric membrane from a second roll of elastomeric membrane and placing said second length of elastomeric membrane over said first length of elastomeric membrane to form an elastomeric laminate;
    (c) stretching said elastomeric laminate to produce a prestressed laminate;
    (d) placing said prestressed laminate over the upper surface of the base;
    (e) emplacing the housing over the base and the prestressed laminate; and
    (f) sealably capturing and connecting the said prestressed laminate and the housing to the base.

11. A method as defined in claim 10 in which said laminate is stretched biaxially.

12. A method as defined in claim 10 including the further step of cutting said prestressed laminate as the housing is emplaced over the base.

13. A method as defined in claim 12 including sealably bonding the housing to the base.

14. A method as defined in claim 13 in which the housing is sonically bonded to the base.

15. A method of making a low profile fluid delivery device for use in infusing medicinal fluid into a patient at a controlled rate having a generally plate like base provided with a fluid outlet and an upper surface including a central portion and an upstanding tongue circumscribing the central portion, a distendable elastomeric membrane superimposed over the base, a housing engageable with the base, said housing having a groove for receiving the tongue of the base, and a cover covering the housing, the method comprising the steps of:

(a) removing a first length of elastomeric membrane from a first roll of elastomeric membrane;

(b) removing a second length of elastomeric membrane from a second roll of elastomeric membrane and placing said second length of elastomeric membrane over said first length of elastomeric membrane to form a first elastomeric laminate;

(c) removing third length of elastomeric membrane from a third roll of elastomeric membrane and placing said third length of elastomeric membrane over said first elastomeric laminate to form a second elastomeric laminate;

(d) stretching said second elastomeric laminate to produce a prestressed second laminate;

(e) placing said second prestressed laminate over the upper surface of the base;

(f) emplacing the housing over the base and said second laminate such that said second laminate is captured between the tongue of the base and the groove of the housing;

(g) cutting said second laminate at a location proximate the upstanding tongue of the base to provide a cut second laminate; and (h) sealably interconnecting said cut second laminate and the cover with the upper surface of the base.

16. A method as defined in claim 15 including the further step of connecting the cover to the housing to form a fluid delivery assembly.

17. A method as defined in claim 16 in which the low profile fluid delivery device includes a flow rate control assembly for controlling fluid flowing from the fluid outlet of the base and in which the method comprises the further step of connecting the flow rate control assembly to the fluid delivery assembly to form a controlled delivery assembly.

18. A method as defined in claim 17 in which the low profile fluid delivery device includes a fluid flow indicator assembly for indicating fluid flow from the fluid outlet of the base and in which the method comprises the further step of connecting the fluid flow indicator assembly to the controlled delivery assembly.

19. A method of making a device for infusing medicinal fluid into a patient at a controlled rate, said device having a plate-like base provided with an upper surface including a central portion, and a peripheral portion circumscribing the central portion, a distendable, elastomeric membrane superimposed over the base and a housing engageable with the base, the method comprising the steps of:

(a) differentially prestressing the membrane;

(b) subsequent to stretching the membrane placing the membrane over the upper surface of the base;

(c) emplacing the housing over the base and the membrane; and (d) sealably connecting the membrane and the housing to the base.

20. A method as defined in claim 19 including the further step of cutting the membrane as the housing is emplaced over the base.

21. A method as defined in claim 20 including sealably bonding the housing to the peripheral portion of the upper surface of the base.

22. A method of making a device for infusing medicinal fluid into a patient at a controlled rate, said device having a plate-like base provided with an upper surface including a central portion, an ullage defining member disposed above the base, a distendable, elastomeric membrane superimposed over the base and the ullage defining member and a housing engageable with the base, the method comprising the steps of:

(a) placing the membrane over the ullage defining member and the upper surface of the base to distend said membrane;

(b) emplacing the housing over the base and the membrane; and (c) sealably connecting the membrane and the housing to the base.

23. A method as defined in claim 22 including the step of differentially prestressing the membrane prior to placing the membrane over the ullage defining member and the base.

24. A method as defined in claim 22 including the step of uniaxially prestressing the membrane prior to placing the membrane over the ullage defining member and the base.

25. A method as defined in claim 22 including the step of biaxially prestressing the membrane prior to placing the membrane over the ullage defining member and the base.

26. A method as defined in claim 22 including the further step of cutting the prestressed membrane as the housing is emplaced over the base.

27. A method as defined in claim 26 including sealably bonding the housing to the peripheral portion of the upper surface of the base.

28. A method of making a device for infusing medicinal fluid into a patient at a controlled rate, said device having a base provided with a fluid inlet, a distendable, elastomeric membrane superimposed over the base, said elastomeric membrane being distendable by fluid introduced into said fluid inlet to form a cooperation with said base a fluid reservoir, the method comprising the steps of:

(a) producing a prestressed membrane from a starting elastomeric membrane by the step of exerting forces on said starting membrane in a manner to produce internal stresses therewithin to form a prestressed membrane;

(b) following the step of forming said prestressed membrane, placing the prestressed membrane over the base; and (c) sealably interconnecting the prestressed membrane with the base.

29. A method as defined in claim 28 in which the device includes a distendable membrane engaging member and in which the method includes the further step of placing the prestressed membrane over the distendable membrane engaging member and the base.

30. A method as defined in claim 28 in which said device includes a cover covering the membrane and in which the method includes the further step of connecting the cover to the base.

\* \* \* \* \*